(12) United States Patent
Otani et al.

(10) Patent No.: US 7,796,257 B2
(45) Date of Patent: Sep. 14, 2010

(54) MEASURING APPARATUS, MEASURING METHOD, AND CHARACTERISTIC MEASUREMENT UNIT

(75) Inventors: Yukitoshi Otani, Musashino (JP); Kazuhiko Oka, Sapporo (JP); Toshitaka Wakayama, Saitama (JP); Atsushi Taniguchi, Fujisawa (JP)

(73) Assignees: National University Corporation Tokyo University of Agriculture and Technology, Tokyo (JP); National University Corporation Hokkaido University, Hokkaido (JP)

( * ) Notice: Subject to any disclaimer, the term of this patent is extended or adjusted under 35 U.S.C. 154(b) by 200 days.

(21) Appl. No.: 12/087,663

(22) PCT Filed: Dec. 27, 2006

(86) PCT No.: PCT/JP2006/326056

§ 371 (c)(1),
(2), (4) Date: Aug. 22, 2008

(87) PCT Pub. No.: WO2007/080790

PCT Pub. Date: Jul. 19, 2007

(65) Prior Publication Data

US 2009/0051916 A1 Feb. 26, 2009

(30) Foreign Application Priority Data

Jan. 13, 2006 (JP) .............................. 2006-006257

(51) Int. Cl.
*G01J 4/00* (2006.01)
(52) U.S. Cl. ...................................... 356/364; 356/367
(58) Field of Classification Search ......... 356/364–370; 250/225
See application file for complete search history.

(56) References Cited

U.S. PATENT DOCUMENTS 6,100,944 A * 8/2000 Sharp et al. ................... 349/19

(Continued)

FOREIGN PATENT DOCUMENTS

JP 2000-502461 10/1997

OTHER PUBLICATIONS

Hiroshi Okabe et al., "New Configuration of Channeled Spectropolarimeter for Snapshot Polarimetric Measurement of Materials", Advanced Characterization Techniques for Optics, Semiconductors, and Nanotechnologies II, pp. 5878OH-1 to 5878OH-8.

(Continued)

*Primary Examiner*—Sang Nguyen
(74) *Attorney, Agent, or Firm*—Posz Law Group, PLC

(57) ABSTRACT

A measuring apparatus includes a light intensity information acquisition section 40 that acquires light intensity information relating to a measurement light containing a given band component, the measurement light having been modulated by optical elements included in an optical system 10 and a measurement target (or a sample 100), and a calculation section 50 that calculates at least one matrix element of a Mueller matrix that indicates the optical characteristics of the measurement target based on the light intensity information relating to the measurement light and a theoretical expression for the light intensity of the measurement light. The light intensity information acquisition section 40 acquires the light intensity information relating to a plurality of the measurement lights obtained from the optical system 10 by changing setting of a principal axis direction of at least one of the optical elements. The calculation section 50 performs a carrier amplitude coefficient calculation process, and a matrix element calculation process that calculates the at least one matrix element based on a carrier amplitude coefficient and the theoretical expression for the carrier amplitude coefficient including the at least one matrix element.

25 Claims, 8 Drawing Sheets

U.S. PATENT DOCUMENTS

| | | | |
|---|---|---|---|
| 6,175,412 B1 | 1/2001 | Drevillion et al. | |
| 6,804,003 B1 * | 10/2004 | Wang et al. | 356/369 |
| 6,924,893 B2 * | 8/2005 | Oldenbourg et al. | 356/369 |
| 6,961,123 B1 * | 11/2005 | Wang et al. | 356/364 |
| 7,084,977 B2 | 8/2006 | Nomura | |
| 7,196,792 B2 * | 3/2007 | Drevillon et al. | 356/367 |
| 7,283,207 B2 | 10/2007 | Nomura | |
| 7,298,480 B2 * | 11/2007 | Garcia-Caurel et al. | 356/364 |
| 2006/0238759 A1 * | 10/2006 | Okabe et al. | 356/369 |

FOREIGN PATENT DOCUMENTS

| | | |
|---|---|---|
| JP | 2005-116732 | 10/2003 |
| JP | 2006-308550 | 12/2005 |
| WO | WO 2006/103953 A1 | 3/2006 |

OTHER PUBLICATIONS

Toshitaka Wakayama et al., "Real-Time Measurement for Birefringence Dispersion Using Double Retarder", Polarization Science and remote Sensing II, pp. 588807-1 yp 588807-6.

Robert W. Collins et al., "Ellipsometry for Thin-Film and Surface Analysis", Analytical Chemistry, vol. 62, No. 17, Sep. 1, 1990, pp. 887-900.

R.M.A. Azzam, "Photopolarimetric Measurement of the Mueller Matrix by Fourier Analysis of a Single Detected Signal", Optics Letters, vol. 2, No. 6, Jun. 1978, pp. 148-150.

David Lara et al., "Polarization Sensitive Imaging Using a Confocal Mueller Matrix Ellipsometer", ICO Topical Meeting on Polarization Optics, 2003, pp. 226-227.

International Search Report of PCT/JP2006/326056 mailed Feb. 6, 2007.

U.S. Appl. No. 11/887,410, filed Mar. 16, 2006, Otani et al.

U.S. Appl. No. 11/922,006, filed Dec. 12, 2007, Otani et al.

* cited by examiner

CORRELATION FUNCTION

MEASURING APPARATUS, MEASURING METHOD, AND CHARACTERISTIC MEASUREMENT UNIT

TECHNICAL FIELD

The present invention relates to a measuring apparatus that calculates matrix elements of a Mueller matrix that indicates the optical characteristics of a measurement target, a measuring method that calculates matrix elements of a Mueller matrix, and a characteristic measurement unit that measures the optical characteristics of a measurement target.

BACKGROUND ART

Technology that analyzes the optical characteristics of a substance by utilizing a Mueller matrix has been known. Several methods have been known for calculating Mueller matrix elements.

Patent Document 1: JP-A-2005-116732
Patent document 2: JP-T-2000-502461
Non-patent Document 1: R. W. Collins and Y. T. Kim, "Ellipsometry for thin-film and Surface analysis", Ann. Chem., 62, 887a-900a (1990)
Non-patent Document 2: R. M. A. Azzam, "Photopolarimetric Measurement of the Mueller Matrix by Fourier Analysis of a Single Detected Signal", Opt. Lett. 2: 148-150 (1978)
Non-patent Document 3: D. Lara and C. Dainty, "Polarization sensitive imaging using a confocal Mueller matrix ellipsometer", ICO topical Meeting on Polarization Optics, 226-227 (2003)

DISCLOSURE OF THE INVENTION

The methods described in the above-mentioned documents have the following problems.

According to the technology disclosed in Patent Document 1, it is difficult to measure the matrix elements of the Mueller matrix with high accuracy.

According to the technology disclosed in Patent Document 2, a high voltage is required for the measurement. Moreover, it is necessary to utilize an expensive modulation element.

According to the technology disclosed in Non-patent Document 1, since at least twelve spectral intensities are required for calculating nine Mueller matrix elements, it is difficult to efficiently measure the Mueller matrix elements.

According to the technology disclosed in Non-patent Document 2, the measurement takes time. Moreover, since at least forty-eight spectral intensities are required for calculating all of the sixteen Mueller matrix elements, it is difficult to efficiently measure the Mueller matrix elements.

According to the technology disclosed in Non-patent Document 3, a high voltage is required for the measurement. Moreover, it is necessary to utilize an expensive optical element. In addition, since four detectors are required, it is difficult to implement a simple device configuration.

An objective of the invention is to provide a measuring apparatus and a measuring method having a relatively simple configuration and capable of calculating Mueller matrix elements by using a small amount of measured data, and a characteristic measurement unit that measures the optical characteristics of a measurement target.

(1) According to the invention, there is provided a measuring apparatus that calculates at least one matrix element among sixteen matrix elements of a Mueller matrix that indicates optical characteristics of a measurement target, the measuring apparatus comprising:

a light intensity information acquisition section that acquires light intensity information relating to a measurement light containing a given band component, the measurement light having been modulated by at least four optical elements included in an optical system and the measurement target; and a calculation section that calculates the at least one matrix element based on the light intensity information relating to the measurement light and a theoretical expression for the light intensity of the measurement light, the at least four optical elements including a first polarizer, a second polarizer, a first carrier retarder, and a second carrier retarder, the first and second carrier retarders having retardations that are known and differ from each other;

the measurement light being obtained by causing a light emitted from a light source to be incident on the measurement target through the first polarizer and the first carrier retarder and causing the light modulated by the measurement target to be incident on a light-receiving section through the second carrier retarder and the second polarizer;

the light intensity information acquisition section acquiring the light intensity information relating to a plurality of the measurement lights obtained from the optical system by changing setting of a principal axis direction of at least one of the at least four optical elements; and the calculation section performing:

a carrier amplitude coefficient calculation process that calculates at least one carrier amplitude coefficient included in the theoretical expression for the light intensity of each of the measurement lights based on a correlation function obtained by analyzing the light intensity information relating to each of the measurement lights; and a matrix element calculation process that calculates the at least one matrix element based on the carrier amplitude coefficient calculated by the carrier amplitude coefficient calculation process and the theoretical expression for the carrier amplitude coefficient including the principal axis directions of the at least four optical elements and the at least one matrix element.

The measuring apparatus according to the invention derives relational expressions that indicate the relationship among the matrix elements of the Mueller matrix.

Specifically, the theoretical expressions for the carrier amplitude coefficients include the matrix elements of the Mueller matrix (see expressions (8a) to (8i) given later). The coefficients included in the theoretical expressions for the carrier amplitude coefficients vary depending on the principal axis directions of the optical elements (see expressions (9a) to (17) given later). Therefore, relational expressions that indicate the relationship among the matrix elements of the Mueller matrix can be derived by substituting the principal axis direction information relating to the optical elements in the theoretical expressions for the carrier amplitude coefficients.

The measuring apparatus according to the invention calculates the matrix elements of the Mueller matrix by solving the relational expressions.

In the invention, the light intensity information relating to a plurality of measurement lights obtained from the optical system by changing setting of the principal axis directions of the optical elements is acquired. For example, in this invention, the light intensity information relating to the first measurement light to the Mth (M is an integer equal to or larger than two) measurement light is acquired. The M measurement lights are respectively obtained from the optical system in which the principal axis directions of the optical elements are set to one of the first to the Mth conditions. The first to Mth conditions differ in the principal axis direction of at least one of the first polarizer, the second polarizer, the first carrier retarder, and the second carrier retarder.

Since the coefficient included in the theoretical expression for the carrier amplitude coefficient depends on the principal axis direction of the optical element, the coefficient of the theoretical expression for the carrier amplitude coefficient changes when the principal axis direction of the optical element changes. Specifically, the number of relational expressions that indicate the relationship among the matrix elements of the Mueller matrix can be increased by acquiring the light intensity information relating to a plurality of measurement lights obtained from the optical system by changing setting of the principal axis directions of the optical elements.

Since the number of matrix elements that can be calculated can be increased by increasing the number of relational expressions that indicate the relationship among the matrix elements of the Mueller matrix, the matrix elements needed can be calculated.

According to the invention, a measuring apparatus that can calculate the matrix elements needed among the sixteen elements of the Mueller matrix can be provided.

(2) According to the invention, there is provided a measuring apparatus that calculates at least one matrix element among sixteen matrix elements of a Mueller matrix that indicates optical characteristics of a measurement target, the measuring apparatus comprising:

an optical system that includes a light source, at least four optical elements, and a light-receiving section that receives a measurement light modulated by the at least four optical elements and the measurement target;

a light intensity information acquisition section that acquires light intensity information relating to the measurement light containing a given band component; and a calculation section that calculates the at least one matrix element based on the light intensity information relating to the measurement light and a theoretical expression for the light intensity of the measurement light, the at least four optical elements including a first polarizer, a second polarizer, a first carrier retarder, and a second carrier retarder, the first and second carrier retarders having retardations that are known and differ from each other;

the optical system causing a light emitted from the light source to be incident on the measurement target through the first polarizer and the first carrier retarder and causing the light modulated by the measurement target to be incident on the light-receiving section through the second carrier retarder and the second polarizer;

the optical system enabling a principal axis direction of at least one of the at least four optical elements to be changed;

the light intensity information acquisition section acquiring the light intensity information relating to a plurality of the measurement lights obtained from the optical system by changing setting of the principal axis direction of at least one of the at least four optical elements; and the calculation section performing:

a carrier amplitude coefficient calculation process that calculates at least one carrier amplitude coefficient included in the theoretical expression for the light intensity of each of the measurement lights based on a correlation function obtained by analyzing the light intensity information relating to each of the measurement lights; and a matrix element calculation process that calculates the at least one matrix element based on the carrier amplitude coefficient calculated by the carrier amplitude coefficient calculation process and the theoretical expression for the carrier amplitude coefficient including the principal axis directions of the at least four optical elements and the at least one matrix element.

The measuring apparatus according to the invention derives relational expressions that indicate the relationship among the matrix elements of the Mueller matrix.

Specifically, the theoretical expressions for the carrier amplitude coefficients include the matrix elements of the Mueller matrix (see expressions (8a) to (8i) given later). The coefficients included in the theoretical expressions for the carrier amplitude coefficients vary depending on the principal axis directions of the optical elements (see expressions (9a) to (17) given later). Therefore, relational expressions that indicate the relationship among the matrix elements of the Mueller matrix can be derived by substituting the principal axis direction information relating to the optical elements in the theoretical expressions for the carrier amplitude coefficients.

The measuring apparatus according to the invention calculates the matrix elements of the Mueller matrix by solving the relational expressions.

In the invention, the light intensity information relating to a plurality of measurement lights obtained from the optical system by changing setting of the principal axis directions of the optical elements is acquired. For example, in this invention, the light intensity information relating to the first measurement light to the Mth (M is an integer equal to or larger than two) measurement light is acquired. The M measurement lights are respectively obtained from the optical system in which the principal axis directions of the optical elements are set to one of the first to the Mth conditions. The first to Mth conditions differ in the principal axis direction of at least one of the first polarizer, the second polarizer, the first carrier retarder, and the second carrier retarder.

Since the coefficient included in the theoretical expression for the carrier amplitude coefficient depends on the principal axis direction of the optical element, the coefficient of the theoretical expression for the carrier amplitude coefficient changes when the principal axis direction of the optical element changes. Specifically, the number of relational expressions that indicate the relationship among the matrix elements of the Mueller matrix can be increased by acquiring the light intensity information relating to a plurality of measurement lights obtained from the optical system by changing setting of the principal axis directions of the optical elements.

Since the number of matrix elements that can be calculated can be increased by increasing the number of relational expressions that indicate the relationship among the matrix elements of the Mueller matrix, the matrix elements needed can be calculated.

According to the invention, a measuring apparatus that can calculate the matrix elements needed among the sixteen elements of the Mueller matrix can be provided.

(3) In the above measuring apparatus, the calculation section may perform the matrix element calculation process based on the carrier amplitude coefficients calculated by the carrier amplitude coefficient calculation process on a plurality of the measurement lights.

In this case, the measuring apparatus calculates matrix elements by utilizing relational expressions derived from the optical system set in one principal axis direction condition and relational expressions derived from the optical system set in another principal axis direction condition (i.e., by solving the relational expressions as simultaneous equations).

As a result, the Mueller matrix elements needed can be calculated.

(4) In the above measuring apparatus, the calculation section may perform the matrix element calculation process based on the carrier amplitude coefficient calculated by the carrier amplitude coefficient calculation process on each of the measurement lights.

In this case, the measuring apparatus calculates matrix elements utilizing relational expressions derived from the optical system set in one principal axis direction condition, and then calculates matrix elements utilizing relational expressions derived from the optical system set in another principal axis direction condition.

As a result, the Mueller matrix elements needed can be calculated.

(5) In the above measuring apparatus, the calculation section may calculate all of the sixteen matrix elements.

All of the sixteen matrix elements of the Mueller matrix can be calculated by appropriately setting the principal axis directions of the optical system.

(6) In the above measuring apparatus, the light intensity information acquisition section may acquire the light intensity information relating to the measurement lights obtained from the optical system by changing the setting of the principal axis direction of at least one of the first polarizer and the first carrier retarder.

(7) In the above measuring apparatus, the light intensity information acquisition section may acquire the light intensity information relating to a plurality of the measurement lights obtained from the optical system set to have a constant angular difference in the principal axis direction between the first polarizer and the first carrier retarder.

This simplifies the calculation process, whereby the processing load of a computer can be reduced.

(8) In the above measuring apparatus, the light intensity information acquisition section may acquire the light intensity information relating to a plurality of the measurement lights obtained from the optical system by changing the setting of the principal axis direction of at least one of the second polarizer and the second carrier retarder.

(9) In the above measuring apparatus, the light intensity information acquisition section may acquire the light intensity information relating to a plurality of the measurement lights obtained from the optical system set to have a constant angular difference in the principal axis direction between the second polarizer and the second carrier retarder.

This simplifies the calculation process, whereby the processing load of a computer can be reduced.

(10) According to the invention, there is provided a measuring apparatus that calculates nine matrix elements among sixteen matrix elements of a Mueller matrix that indicates optical characteristics of a measurement target, the measuring apparatus comprising:

a light intensity information acquisition section that acquires light intensity information relating to a measurement light containing a given band component, the measurement light having been modulated by at least four optical elements included in an optical system and the measurement target, the at least four optical elements being set to have a given angular difference in principal axis direction; and a calculation section that calculates the nine matrix elements based on the light intensity information relating to the measurement light and a theoretical expression for the light intensity of the measurement light, the at least four optical elements including a first polarizer, a second polarizer, a first carrier retarder, and a second carrier retarder, the first and second carrier retarders having retardations that are known and differ from each other;

the measurement light being obtained by causing a light emitted from a light source to be incident on the measurement target through the first polarizer and the first carrier retarder and causing the light modulated by the measurement target to be incident on a light-receiving section through the second carrier retarder and the second polarizer; and the calculation section performing:

a carrier amplitude coefficient calculation process that calculates all of nine carrier amplitude coefficients included in the theoretical expression for the light intensity of the measurement light based on a correlation function obtained by analyzing the light intensity information; and a matrix element calculation process that calculates the nine matrix elements based on the nine carrier amplitude coefficients calculated by the carrier amplitude coefficient calculation process and the theoretical expression for the carrier amplitude coefficients including the principal axis directions of the at least four optical elements and the nine matrix elements.

The measuring apparatus according to the invention calculates nine matrix elements among the sixteen matrix elements of the Mueller matrix by using one piece of light intensity information obtained by one measurement.

Specifically, all of the nine carrier amplitude coefficients included in the theoretical expression for the light intensity of the measurement light are calculated. The principal axis directions of the optical elements are set so that only nine matrix elements appear in the theoretical expressions for the nine carrier amplitude coefficients. Therefore, nine relational expressions including the nine matrix elements as unknown quantities can be derived. The nine matrix elements can be calculated by solving the nine relational expressions.

Specifically, nine matrix elements among the sixteen matrix elements of the Mueller matrix can be calculated by using one piece of light intensity information obtained by one measurement. Therefore, the measuring apparatus according to the invention can calculate the matrix elements needed by using a small amount of data. Moreover, the measuring apparatus according to the invention can efficiently calculate the matrix elements since the principal axis directions of the optical elements need not be changed.

(11) According to the invention, there is provided a measuring apparatus that calculates nine matrix elements among sixteen matrix elements of a Mueller matrix that indicates optical characteristics of a measurement target, the measuring apparatus comprising:

an optical system that includes a light source, at least four optical elements, and a light-receiving section that receives a measurement light modulated by the at least four optical elements and the measurement target;

a light intensity information acquisition section that acquires light intensity information relating to the measurement light containing a given band component; and a calculation section that calculates the nine matrix elements based on the light intensity information relating to the measurement light and a theoretical expression for the light intensity of the measurement light, the at least four optical elements including a first polarizer, a second polarizer, a first carrier retarder, and a second carrier retarder, the first and second carrier retarders having retardations that are known and differ from each other;

the optical system causing a light emitted from the light source to be incident on the measurement target through the first polarizer and the first carrier retarder and causing the light modulated by the measurement target to be incident on the light-receiving section through the second carrier retarder and the second polarizer;

the optical system being set so that the four optical elements have a given angular difference in principal axis direction; and the calculation section performing:

a carrier amplitude coefficient calculation process that calculates all of nine carrier amplitude coefficients included in the theoretical expression for the light intensity of the measurement light based on a correlation function obtained by analyzing the light intensity information; and a matrix element calculation process that calculates the nine matrix elements based on the nine carrier amplitude coefficients calculated by the carrier amplitude coefficient calculation process and the theoretical expression for the carrier amplitude coefficients including the principal axis directions of the at least four optical elements and the nine matrix elements.

The measuring apparatus according to the invention calculates nine matrix elements among the sixteen matrix elements of the Mueller matrix by using one piece of light intensity information obtained by one measurement.

Specifically, all of the nine carrier amplitude coefficients included in the theoretical expression for the light intensity of the measurement light are calculated. The principal axis directions of the optical elements are set so that only nine matrix elements appear in the theoretical expressions for the nine carrier amplitude coefficients. Therefore, nine relational expressions including the nine matrix elements as unknown quantities can be derived. The nine matrix elements can be calculated by solving the nine relational expressions.

Specifically, nine matrix elements among the sixteen matrix elements of the Mueller matrix can be calculated by using one piece of light intensity information obtained by one measurement. Therefore, the measuring apparatus according to the invention can calculate the matrix elements needed by using a small amount of data. Moreover, the measuring apparatus according to the invention can efficiently calculate the matrix elements since the principal axis directions of the optical elements need not be changed.

(12) In the above measuring apparatus, the light intensity information acquisition section may acquire the light intensity information relating to the measurement light obtained from the optical system that is set so that the angular difference in the principal axis direction between the at least four optical elements is a multiple of 45°.

This reduces the calculation load.

(13) In the above measuring apparatus, the light intensity information acquisition section may acquire the light intensity information relating to the measurement light obtained from the optical system set so that the angular difference in the principal axis direction between the first polarizer and the first carrier retarder is a multiple of 45° by an odd number, the angular difference in the principal axis direction between the second polarizer and the second carrier retarder is a multiple of 450° by an odd number, and the angular difference in the principal axis direction between the first carrier retarder and the second carrier retarder is a multiple of 45°.

According to this measuring apparatus, only nine matrix elements appear in the nine theoretical expressions for the carrier amplitude coefficients included in the theoretical expression for the light intensity of the measurement light obtained by one measurement. According to this measuring apparatus, nine matrix elements can be calculated based only on one piece of light intensity information obtained by one measurement.

(14) The above measuring apparatus may further comprise a detection section that detects principal axis direction information relating to the at least four optical elements, wherein the calculation section may perform the carrier amplitude coefficient calculation process by utilizing the principal axis direction information detected by the detection section.

(15) The above measuring apparatus may further comprise an actuator that changes the principal axis direction of at least one of the at least four optical elements.

(16) In the above measuring apparatus, the light emitted from the light source may contain a given band component.

(17) According to the invention, there is provided a measuring apparatus that calculates all of sixteen matrix elements of a Mueller matrix that indicates optical characteristics of a measurement target, the measuring apparatus comprising:

a light intensity information acquisition section that acquires light intensity information relating to a measurement light containing a given band component, the measurement light having been modulated by a plurality of optical elements included in an optical system and the measurement target; and a calculation section that calculates all of the sixteen matrix elements based on the light intensity information relating to the measurement light and a theoretical expression for the light intensity of the measurement light, the light intensity information acquisition section acquiring the light intensity information relating to a plurality of the measurement lights obtained from the optical system by changing setting of a principal axis direction of at least one of the optical elements; and the calculation section performing:

a carrier amplitude coefficient calculation process that calculates at least one carrier amplitude coefficient included in the theoretical expression for the light intensity of each of the measurement lights based on a correlation function obtained by analyzing the light intensity information relating to each of the measurement lights; and a matrix element calculation process that calculates all of the sixteen matrix elements based on the carrier amplitude coefficient calculated by the carrier amplitude coefficient calculation process and the theoretical expression for the carrier amplitude coefficient including the principal axis directions of a plurality of the optical elements and at least one of the matrix elements.

The measuring apparatus according to the invention derives relational expressions that indicate the relationship among the matrix elements of the Mueller matrix.

Specifically, the theoretical expressions for the carrier amplitude coefficients include the matrix elements of the Mueller matrix (see expressions (8a) to (8i) given later). The coefficients included in the theoretical expressions for the carrier amplitude coefficients vary depending on the principal axis directions of the optical elements (see expressions (9a) to (17) given later). Therefore, relational expressions that indicate the relationship among the matrix elements of the Mueller matrix can be derived by substituting the principal axis direction information relating to the optical elements in the theoretical expressions for the carrier amplitude coefficients.

The measuring apparatus according to the invention calculates the matrix elements of the Mueller matrix by solving the relational expressions.

In the invention, the light intensity information relating to a plurality of measurement lights obtained from the optical system by changing setting of the principal axis directions of the optical elements is acquired. For example, in this invention, the light intensity information relating to the first measurement light to the Mth (M is an integer equal to or larger than two) measurement light is acquired. The M measurement lights are respectively obtained from the optical system in which the principal axis directions of the optical elements are set to one of the first to the Mth conditions. The first to Mth conditions differ in the principal axis direction of at least one of the optical elements.

Since the coefficient included in the theoretical expression for the carrier amplitude coefficient depends on the principal axis direction of the optical element, the coefficient of the theoretical expression for the carrier amplitude coefficient changes when the principal axis direction of the optical element changes. Specifically, the number of relational expressions that indicate the relationship among the matrix elements of the Mueller matrix can be increased by acquiring the light intensity information relating to a plurality of measurement lights obtained from the optical system by changing setting of the principal axis directions of the optical elements.

Since the number of matrix elements that can be calculated can be increased by increasing the number of relational expressions that indicate the relationship among the matrix elements of the Mueller matrix, the matrix elements needed can be calculated.

According to the invention, a measuring apparatus that can calculate the matrix elements needed among the sixteen elements of the Mueller matrix can be provided.

(18) An optical characteristic measurement unit according to the invention comprises any of the above-described measuring apparatuses.

The optical characteristic measurement unit may be configured to calculate the optical characteristic elements of the measurement target by utilizing the matrix elements of the Mueller matrix. In this case, the optical characteristic measurement unit may be configured to calculate optical characteristic elements of the measurement target such as retardation, depolarization, and dichroism.

(19) According to the invention, there is provided a measuring method for calculating at least one matrix element among sixteen matrix elements of a Mueller matrix that indicates optical characteristics of a measurement target, the measuring method comprising:

a light intensity information acquisition step that acquires light intensity information relating to a measurement light containing a given band component, the measurement light having been modulated by at least four optical elements included in an optical system and the measurement target; and a calculation step that calculates the at least one matrix element based on the light intensity information relating to the measurement light and a theoretical expression for the light intensity of the measurement light, the at least four optical elements including a first polarizer, a second polarizer, a first carrier retarder, and a second carrier retarder, the first and second carrier retarders having retardations that are known and differ from each other;

the measurement light being obtained by causing a light emitted from a light source to be incident on the measurement target through the first polarizer and the first carrier retarder and causing the light modulated by the measurement target to be incident on a light-receiving section through the second carrier retarder and the second polarizer;

the light intensity information acquisition step acquiring the light intensity information relating to a plurality of the measurement lights obtained from the optical system by changing setting of a principal axis direction of at least one of the at least four optical elements; and the calculation step including:

a carrier amplitude coefficient calculation process that calculates at least one carrier amplitude coefficient included in the theoretical expression for the light intensity of each of the measurement lights based on a correlation function obtained by analyzing the light intensity information relating to each of the measurement lights; and a matrix element calculation process that calculates the at least one matrix element based on the carrier amplitude coefficient calculated by the carrier amplitude coefficient calculation process and the theoretical expressions for the carrier amplitude coefficient including the principal axis directions of the at least four optical elements and the at least one matrix element.

The measuring method according to the invention derives relational expressions that indicate the relationship among the matrix elements of the Mueller matrix.

Specifically, the theoretical expressions for the carrier amplitude coefficients include the matrix elements of the Mueller matrix (see expressions (8a) to (8i) given later). The coefficients included in the theoretical expressions for the carrier amplitude coefficients vary depending on the principal axis directions of the optical elements (see expressions (9a) to (17) given later). Therefore, relational expressions that indicate the relationship among the matrix elements of the Mueller matrix can be derived by substituting the principal axis direction information relating to the optical elements in the theoretical expressions for the carrier amplitude coefficients.

The measuring method according to the invention calculates the matrix elements of the Mueller matrix by solving the relational expressions.

In the invention, the light intensity information relating to a plurality of measurement lights obtained from the optical system by changing setting of the principal axis directions of the optical elements is acquired. For example, in this invention, the light intensity information relating to the first measurement light to the Mth (M is an integer equal to or larger than two) measurement light is acquired. The M measurement lights are respectively obtained from the optical system in which the principal axis directions of the optical elements are set to the first to the Mth conditions. The first to Mth conditions differ in the principal axis direction of at least one of the first polarizer, the second polarizer, the first carrier retarder, and the second carrier retarder.

Since the coefficient included in the theoretical expression for the carrier amplitude coefficient depends on the principal axis direction of the optical element, the coefficient of the theoretical expression for the carrier amplitude coefficient changes when the principal axis direction of the optical element changes. Specifically, the number of relational expressions that indicate the relationship among the matrix elements of the Mueller matrix can be increased by acquiring the light intensity information relating to a plurality of measurement lights obtained from the optical system by changing setting of the principal axis directions of the optical elements.

Since the number of matrix elements that can be calculated can be increased by increasing the number of relational expressions that indicate the relationship among the matrix elements of the Mueller matrix, the matrix elements needed can be calculated.

According to the invention, a measuring method that can calculate the matrix elements needed among the sixteen elements of the Mueller matrix can be provided.

(20) In the calculation step of the above measuring method, the matrix element calculation process may be performed based on the carrier amplitude coefficients calculated by the carrier amplitude coefficient calculation process on a plurality of the measurement lights.

In this case, the measuring method calculates the matrix elements by utilizing relational expressions derived from the optical system set in one principal axis direction condition and relational expressions derived from the optical system set in another principal axis direction condition (i.e., by solving the relational expressions as simultaneous equations).

As a result, the Mueller matrix elements needed can be calculated.

(21) In the calculation step of the above measuring method, the matrix element calculation process may be performed based on the carrier amplitude coefficient calculated by the carrier amplitude coefficient calculation process on each of the measurement lights.

In this case, the measuring method calculates matrix elements utilizing relational expressions derived from the optical system set in one principal axis direction condition, and then calculates matrix elements utilizing relational expressions derived from the optical system set in another principal axis direction condition.

As a result, the Mueller matrix elements needed can be calculated.

(22) In the above measuring method, the calculation step may calculate all of the sixteen matrix elements.

All of the sixteen matrix elements of the Mueller matrix can be calculated by appropriately setting the principal axis directions of the optical system.

(23) According to the invention, there is provided a measuring method for calculating nine matrix elements among sixteen matrix elements of a Mueller matrix that indicates optical characteristics of a measurement target, the measuring method comprising:

a light intensity information acquisition step that acquires light intensity information relating to a measurement light containing a given band component, the measurement light having been modulated by at least four optical elements included in an optical system and the measurement target, the at least four optical elements being set to have a given angular difference in principal axis direction; and a calculation step that calculates the nine matrix elements based on the light intensity information relating to the measurement light and a theoretical expression for the light intensity of the measurement light, the at least four optical elements including a first polarizer, a second polarizer, a first carrier retarder, and a second carrier retarder, the first and second carrier retarders having retardations that are known and differ from each other;

the measurement light being obtained by causing a light emitted from a light source to be incident on the measurement target through the first polarizer and the first carrier retarder and causing the light modulated by the measurement target to be incident on a light-receiving section through the second carrier retarder and the second polarizer; and the calculation step including:

a carrier amplitude coefficient calculation process that calculates all of nine carrier amplitude coefficients included in the theoretical expression for the light intensity of the measurement light based on a correlation function obtained by analyzing the light intensity information; and a matrix element calculation process that calculates the nine matrix elements based on the nine carrier amplitude coefficients calculated by the carrier amplitude coefficient calculation process and the theoretical expression for the carrier amplitude coefficients including the principal axis directions of the at least four optical elements and the nine matrix elements.

The measuring method according to the invention calculates nine matrix elements among the sixteen matrix elements of the Mueller matrix by using one piece of light intensity information obtained by one measurement.

Specifically, all of the nine carrier amplitude coefficients included in the theoretical expression for the light intensity of the measurement light are calculated. The principal axis directions of the optical elements are set so that only nine matrix elements appear in the theoretical expressions for the nine carrier amplitude coefficients. Therefore, nine relational expressions including the nine matrix elements as unknown quantities can be derived. The nine matrix elements can be calculated by solving the nine relational expressions.

Specifically, nine matrix elements among the sixteen matrix elements of the Mueller matrix can be calculated by using one piece of light intensity information obtained by one measurement. Therefore, the measuring method according to the invention can calculate the matrix elements needed by using a small amount of data. Moreover, the measuring method according to the invention can efficiently calculate the matrix elements since the principal axis directions of the optical elements need not be changed.

(24) In the above measuring method, the light emitted from the light source may contain a given band component.

(25) According to the invention, there is provided a measuring method for calculating all of sixteen matrix elements of a Mueller matrix that indicates optical characteristics of a measurement target, the measuring method comprising:

a light intensity information acquisition step that acquires light intensity information relating to a measurement light containing a given band component, the measurement light having been modulated by a plurality of optical elements included in an optical system and the measurement target; and a calculation step that calculates the sixteen matrix elements based on the light intensity information relating to the measurement light and a theoretical expression for the light intensity of the measurement light, the light intensity information acquisition step acquiring the light intensity information relating to a plurality of the measurement lights obtained from the optical system by changing setting of a principal axis direction of at least one of the optical elements; and the calculation step including:

a carrier amplitude coefficient calculation process that calculates at least one carrier amplitude coefficient included in the theoretical expression for the light intensity of each of the measurement lights based on a correlation function obtained by analyzing the light intensity information relating to each of the measurement lights; and a matrix element calculation process that calculates all of the sixteen matrix elements based on the carrier amplitude coefficients calculated by the carrier amplitude coefficient calculation process and the theoretical expression for the carrier amplitude coefficient including the principal axis directions of the optical elements and at least one of the matrix elements.

The measuring method according to the invention derives relational expressions that indicate the relationship among the matrix elements of the Mueller matrix.

Specifically, the theoretical expressions for the carrier amplitude coefficients include the matrix elements of the Mueller matrix (see expressions (8a) to (8i) given later). The coefficients included in the theoretical expressions for the carrier amplitude coefficients vary depending on the principal axis directions of the optical elements (see expressions (9a) to (17) given later). Therefore, relational expressions that indicate the relationship among the matrix elements of the Mueller matrix can be derived by substituting the principal axis direction information relating to the optical elements in the theoretical expressions for the carrier amplitude coefficients.

The measuring method according to the invention calculates the matrix elements of the Mueller matrix by solving the relational expressions.

In the invention, the light intensity information relating to a plurality of measurement lights obtained from the optical system by changing setting of the principal axis directions of the optical elements is acquired. For example, in this invention, the light intensity information relating to the first measurement light to the Mth (M is an integer equal to or larger than two) measurement light is acquired. The M measurement lights are respectively obtained from the optical system in which the principal axis directions of the optical elements are set to the first to the Mth conditions. The first to Mth conditions differ in the principal axis direction of at least one of the optical elements.

Since the coefficient included in the theoretical expression for the carrier amplitude coefficient depends on the principal axis direction of the optical element, the coefficient of the theoretical expression for the carrier amplitude coefficient changes when the principal axis direction of the optical element changes. Specifically, the number of relational expressions that indicate the relationship among the matrix elements of the Mueller matrix can be increased by acquiring the light intensity information relating to a plurality of measurement lights obtained from the optical system by changing setting of the principal axis directions of the optical elements.

Since the number of matrix elements that can be calculated can be increased by increasing the number of relational expressions that indicate the relationship among the matrix elements of the Mueller matrix, the matrix elements needed can be calculated.

According to the invention, a measuring method that can calculate the matrix elements needed among the sixteen elements of the Mueller matrix can be provided.

BEST MODE FOR CARRYING OUT THE INVENTION

Embodiments of the invention are described below with reference to the drawings.

A measuring apparatus according to one embodiment of the invention calculates at least one matrix element among the sixteen matrix elements of a Mueller matrix that indicates the optical characteristics of a measurement target. Note that the measuring apparatus according to the invention may form an optical characteristic measurement unit that measures the optical characteristics of a measurement target.

First Embodiment

A measuring apparatus 1 that can calculate all of the sixteen matrix elements of a Mueller matrix that indicates the optical characteristics of a sample 100 (i.e., measurement target) is described below as a measuring apparatus according to a first embodiment to which the invention is applied.

(1) Device Configuration

Figure 1:
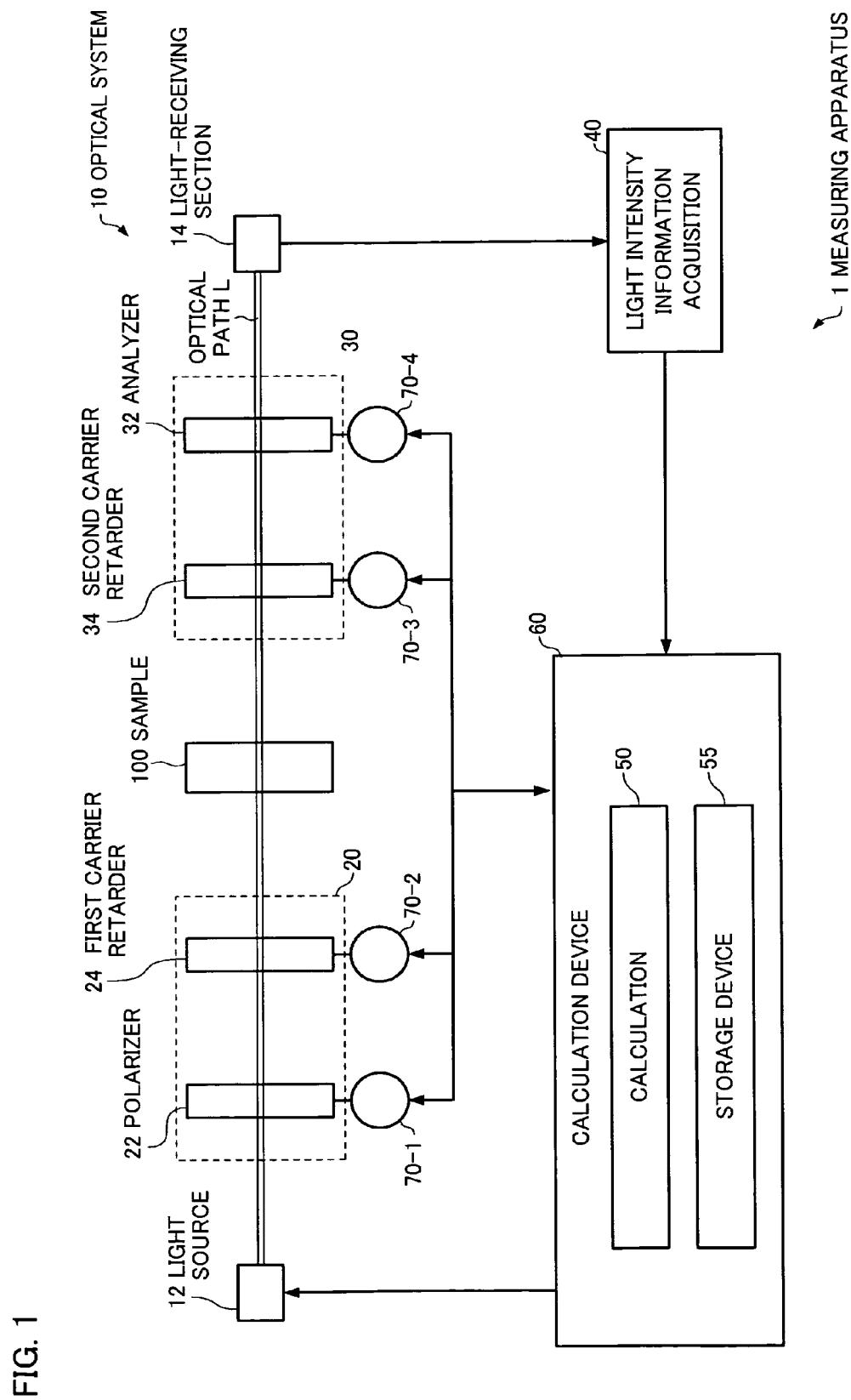
FIG. 1 is a diagram illustrative of a measuring apparatus according to one embodiment of the invention.

FIG. 1 shows the measuring apparatus 1.

The measuring apparatus 1 according to this embodiment calculates the matrix elements of a Mueller matrix that indicates the optical characteristics of the sample 100 (i.e., measurement target). The measuring apparatus 1 includes a light intensity information acquisition section 40 and a calculation section 50. The light intensity information acquisition section 40 acquires light intensity information relating to measurement light modulated by an optical element included in an optical system 10 and the sample 100. The calculation section 50 performs a calculation process that calculates the Mueller matrix elements based on the light intensity information relating to the measurement light and a theoretical expression for the light intensity of the measurement light. The sample 100 may be a substance that allows light to pass through, or may be a substance that reflects light.

The device configuration of the measuring apparatus 1 is described below.

1-1: Optical System 10

The optical system 10 includes a light source 12 and a light-receiving section 14. The optical system 10 also includes a polarizer 22, a first carrier retarder 24, a second carrier retarder 34, and an analyzer 32 which are optical elements provided in an optical path L that connects the light source 12 and the light-receiving section 14. The optical system 10 is configured so that light emitted from the light source 12 is incident on the sample 100 through the polarizer 22 and the first carrier retarder 24, and the light modulated by the sample 100 is incident on the light-receiving section 14 through the second carrier retarder 34 and the analyzer 32.

As shown in FIG. 1, the optical system 10 according to this embodiment is configured so that light that has passed through the sample 100 is incident on the second carrier retarder 34. Note that the optical system according to the invention may be configured so that light reflected by the sample 100 is incident on the second carrier retarder 34 (not shown).

The light source 12 is a device that produces and emits light. In this embodiment, a device that emits light containing a given wavelength (wave number σ) band component may be utilized as the light source 12. For example, a white light source such as a halogen lamp may be used as the light source 12.

The polarizer 22 is an incident-side polarizer that makes a pair with the analyzer 32 and linearly polarizes light emitted from the light source 12.

The first carrier retarder 24 and the second carrier retarder 34 are optical elements that make a pair and are disposed on either side of the sample 100. Specifically, the optical system 10 is configured so that the sample 100 can be provided between the first carrier retarder 24 and the second carrier retarder 34.

The first carrier retarder 24 and the second carrier retarder 34 are optical elements of which the retardation differs depending on the wavelength of light that passes through.

Therefore, the polarization state of light that has passed through the first carrier retarder 24 and the second carrier retarder 34 changes depending on its wavelength.

The first carrier retarder 24 and the second carrier retarder 34 may be formed using a high-order retardation plate, for example. The retardations of the first carrier retarder 24 and the second carrier retarder 34 are known and differ from each other. Specifically, when the retardation of the first carrier retarder 24 is referred to as $\phi_1(\sigma)$ and the retardation of the second carrier retarder 34 is referred to as $\phi_2(\sigma)$, $\phi_1(\sigma)$ and $\phi_2(\sigma)$ are set to be different values. Note that the retardations of the first carrier retarder 24 and the second carrier retarder 34 need not be known when performing a light intensity information acquisition process. The retardations of the first carrier retarder 24 and the second carrier retarder 34 are used when performing the calculation process.

The analyzer 32 is an exit-side polarizer that linearly polarizes a light modulated by the sample 100 (light that has passed through the second carrier retarder 34). The analyzer 32 may be referred to as a polarizer that makes a pair with the polarizer 22. Specifically, the polarizer 22 may be referred to as a first polarizer, and the analyzer 32 may be referred to as a second polarizer.

The optical system 10 is configured so that the principal axis direction of at least one of the polarizer 22, the first carrier retarder 24, the second carrier retarder 34, and the analyzer 32 can be changed. Note that the optical system 10 may be configured so that the principal axis directions of all of these optical elements can be changed. For example, the optical system 10 may be configured so that the principal axis directions of the polarizer 22, the first carrier retarder 24, the second carrier retarder 34, and the analyzer 32 can be changed by using an actuator.

In the optical system 10, the polarizer 22 and the first carrier retarder 24 positioned on the incident side of the sample 100 may form a polarization modulation unit 20. The second carrier retarder 34 and the analyzer 32 positioned on the exit side of the sample 100 may form a polarization analysis unit 30. The optical elements (i.e., polarizer 22, first carrier retarder 24, second carrier retarder 34, and analyzer 32) and the sample 100 may be collectively referred to as a polarization optical system.

The optical system 10 may further include a light guide (not shown). The light guide may be an optical element (optical device) that vertically and/or horizontally enlarges light emitted from the light source 12 corresponding to the sample 100. A measurement process on the sample 100 can be efficiently performed by utilizing the light guide.

The light-receiving section 14 receives a measurement light. The term "measurement light" used herein refers to a light emitted from the light source 12 and modulated by the optical elements included in the optical system 10 and the sample 100 (polarization optical system). The measurement light may be light containing a given band component. When the light source 12 emits light containing a band component, the measurement light contains the band component.

Figure 2:
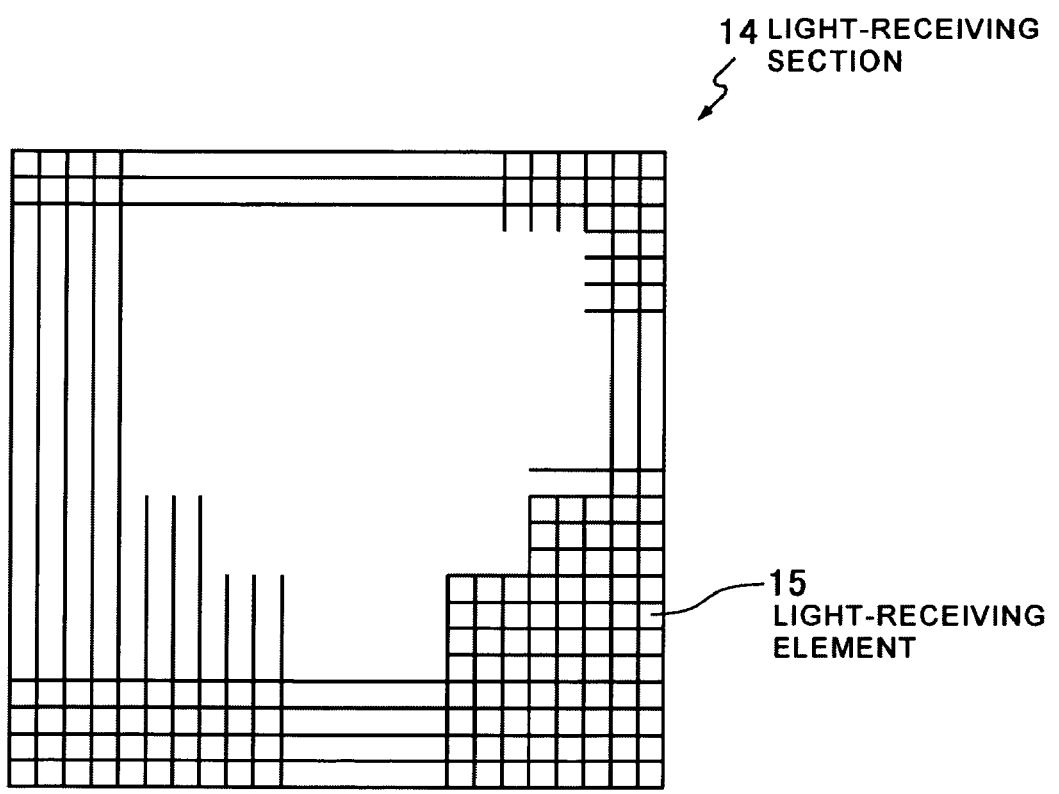
FIG. 2 is a diagram illustrative of a measuring apparatus according to one embodiment of the invention.

The light-receiving section 14 may include a plurality of light-receiving elements 15. As shown in FIG. 2, the light-receiving elements 15 may be arranged in a plane (i.e., two-dimensionally). In this case, the light-receiving elements 15 may form a light-receiving surface. The light intensity information acquisition section 40 may acquire the light intensity information relating to the measurement light incident on each light-receiving element 15. A CCD may be utilized as the light-receiving section 14, for example.

The light-receiving section 14 may further include a spectroscope. In this case, the light-receiving section 14 is configured so that the spectroscope disperses the measurement light into a spectrum and the dispersed measurement light is incident on each light-receiving element 15. Specifically, when the light-receiving section 14 includes the spectroscope and the light-receiving elements 15, the spectroscope is disposed on the upstream side (on the side of the light source 12) of the light-receiving elements 15. A prism or a grating may be utilized as the spectroscope, for example.

The measurement light is incident on the light-receiving section as follows.

Light containing a given band component emitted from the light source 12 passes through the polarizer 22 and the first carrier retarder 24, as shown in FIG. 1. The retardation of the first carrier retarder 24 differs depending on the wavelength of light that passes through, as described above. Therefore, the polarization state of light that has passed through the first carrier retarder 24 changes depending on its wavelength. Since the first carrier retarder 24 is a high-order retardation plate, the polarization state of light that has passed through the first carrier retarder 24 shows a periodic change with respect to the wavelength.

The light that has passed through the first carrier retarder 24 passes through the sample 100 (or is reflected by the sample 100) so that the polarization state further changes.

The light that has passed through the sample 100 passes through the second carrier retarder 34 positioned on the downstream side of the sample 100. The polarization state of the light further changes due to the second carrier retarder 34.

The light that has passed through these optical elements passes through the analyzer 32 and is incident on the light-receiving section 14 as the measurement light.

Specifically, the measurement light incident on the light-receiving section 14 may be referred to as light that is frequency-modulated with respect to the wavelength (wave number $\sigma$). The measurement light incident on the light-receiving section 14 may be referred to as light that contains a given band component (wave number $\sigma$) and differs in modulation state corresponding to each wave number. Since the optical system 10 includes the carrier retarder, the intensity of the measurement light incident on the light-receiving section 14 periodically changes with respect to the wave number without rotating the optical element included in the optical system 10 (see FIG. 3A).

1-2: Light Intensity Information Acquisition Section 40

The light intensity information acquisition section 40 acquires the light intensity information relating to the measurement light containing a given band component that has been modulated by the optical elements included in the optical system 10 and the sample 100.

Figure 3A:
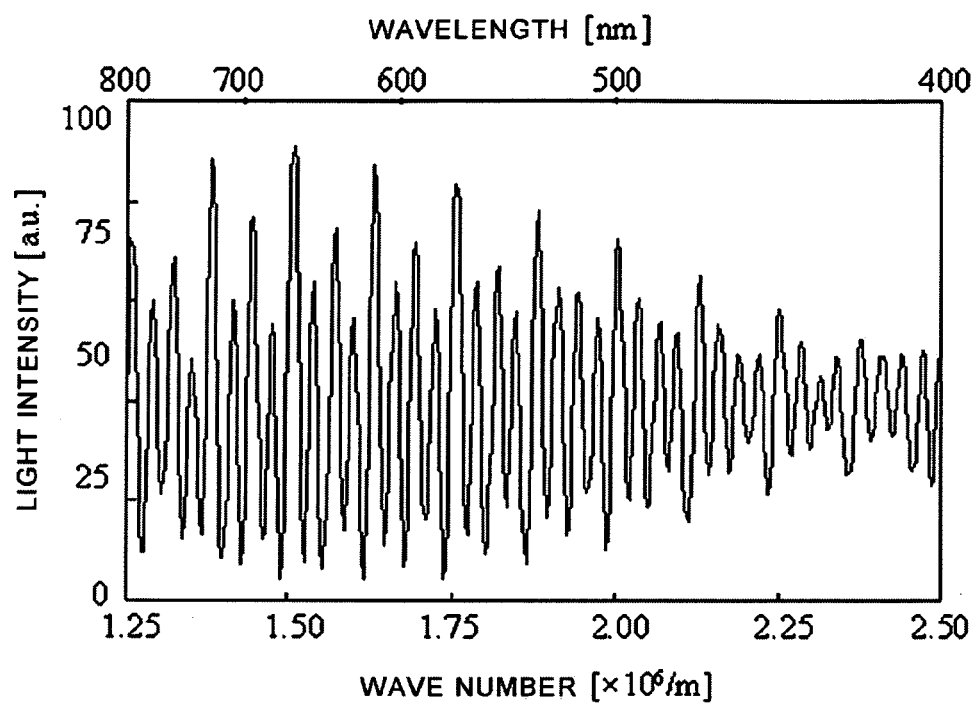
FIG. 3 is a diagram showing an example of light intensity information.

The light intensity information acquisition section 40 acquires the light intensity information as the light intensity $P(\sigma)$ corresponding to the wave number $\sigma$, as shown in FIG. 3A. Specifically, the light intensity depends on the wavelength. When a light source that emits light containing a band component is utilized as the light source, the measurement light also contains the band component. Therefore, the light intensity $P(\sigma)$ corresponding to the wave number $\sigma$ (dependent on the wavelength) can be acquired by dispersing the measurement light into a spectrum and measuring the light intensity corresponding to each wave number $\sigma$, as shown in FIG. 3A. The optical system 10 includes the carrier retarders (first carrier retarder 24 and second carrier retarder 34). Therefore, the intensity of the measurement light modulated by the optical system 10 and incident on the light-receiving section 14 periodically changes with respect to the wavelength (wave number), as shown in FIG. 3A. Specifically, an analyzable measurement light can be obtained from the optical system 10 without rotating the optical elements, as shown in FIG. 3A. The light intensity P(σ) may be acquired by photoelectrically converting the measurement light that is incident on the light-receiving section 14 (light-receiving element 15), for example.

Figure 3B:
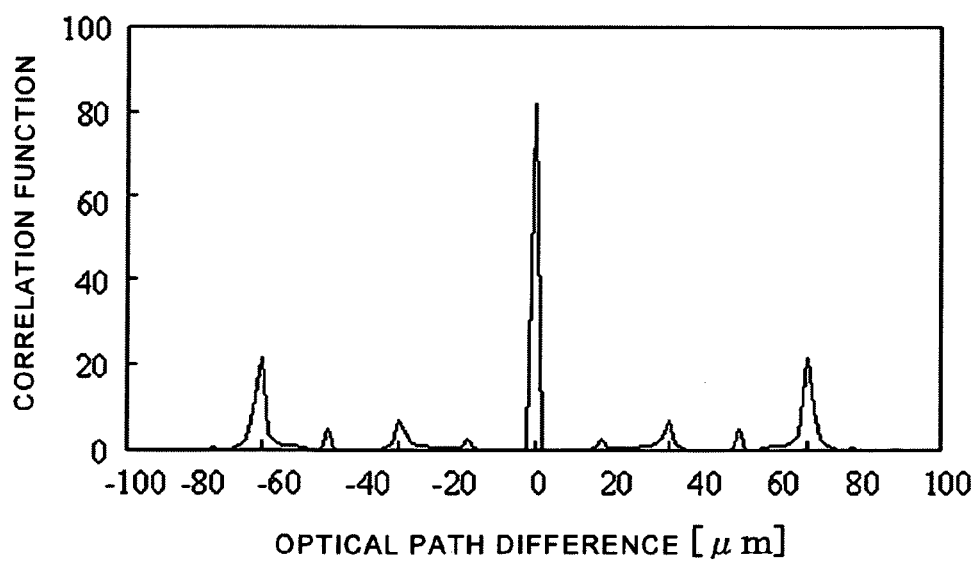

Alternatively, the light intensity information acquisition section 40 may analyze the light intensity P(σ) shown in FIG. 3A to obtain a correlation function shown in FIG. 3B.

The light intensity information acquisition section 40 acquires the light intensity information relating to a plurality of measurement lights obtained from the optical system 10 by changing setting of the principal axis direction of at least one of the polarizer 22, the first carrier retarder 24, the second carrier retarder 34, and the analyzer 32.

Specifically, the light intensity information acquisition section 40 acquires the light intensity information relating to a plurality of measurement lights. The measurement lights are obtained from the optical system 10 by changing setting of the principal axis direction of at least one of the optical elements (polarizer 22, first carrier retarder 24, second carrier retarder 34, and analyzer 32).

Specifically, the light intensity information acquisition section 40 acquires the first light intensity information to the Mth (M is an integer equal to or larger than two) light intensity information (i.e., M pieces of light intensity information). The first light intensity information to the Mth light intensity information indicate the light intensities of the measurement lights respectively obtained from the optical system 10 set to one of first to Mth principal axis direction conditions. The first to Mth principal axis direction conditions differ in the principal axis direction of at least one of the optical elements (polarizer 22, first carrier retarder 24, second carrier retarder 34, and analyzer 32).

The light intensity information acquired by the light intensity information acquisition section 40 is stored in a storage device 55 provided in a calculation device 60. The storage device 55 stores a plurality of pieces of light intensity information corresponding to each setting condition for the optical system 10 (i.e., principal axis direction setting of the polarizer 22, the first carrier retarder 24, the second carrier retarder 34, and the analyzer 32). For example, the storage device 55 stores the first light intensity information to the Mth light intensity information corresponding to the first to the Mth principal axis direction conditions (principal axis direction information).

1-3: Calculation Section 50

The calculation section 50 performs the calculation process that calculates the Mueller matrix elements based on the light intensity information relating to the measurement light and a theoretical expression for the light intensity of the measurement light. Specifically, the calculation section 50 calculates the Mueller matrix elements.

The calculation section 50 performs a carrier amplitude coefficient calculation process that calculates a carrier amplitude coefficient from the light intensity information relating to the measurement light, and a matrix element calculation process that calculates the matrix elements based on the carrier amplitude coefficient and the theoretical expressions for the carrier amplitude coefficients.

The details of these calculation processes are described later. The carrier amplitude coefficient calculation process is a process that calculates at least one carrier amplitude coefficient based on the correlation function (see FIG. 3B) obtained by analyzing the light intensity information relating to the measurement light. The matrix element calculation process is a process that calculates the Mueller matrix elements based on the carrier amplitude coefficient calculated by the carrier amplitude coefficient calculation process and the theoretical expressions for the carrier amplitude coefficients.

1-4: Calculation Device 60

The measuring apparatus 1 may include the calculation device 60. In this case, the calculation device 60 includes the calculation section 50. The calculation device 60 also includes the storage device 55. The storage device 55 may have a function of temporarily storing various types of data calculated by the calculation section 50.

The measuring apparatus 1 can perform a process utilizing a computer using the calculation device 60 (calculation section 50). The term "computer" used herein refers to a physical device (system) that includes a processor (processing section: CPU or the like), a memory (storage section), an input device, and an output device as basic elements.

Figure 4:
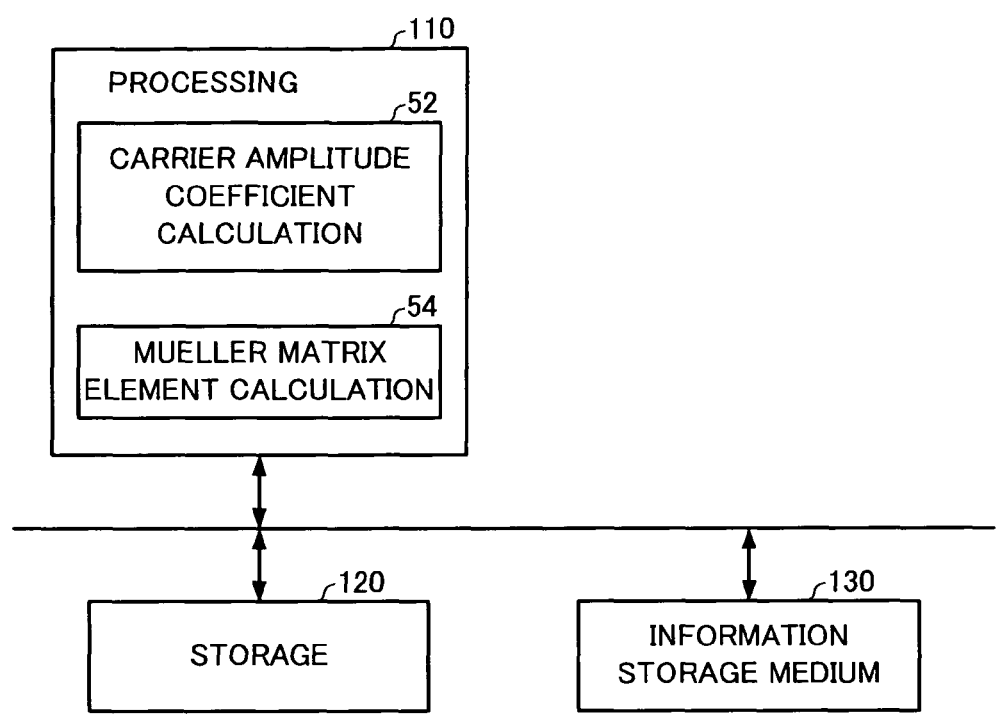
FIG. 4 is a diagram illustrative of a measuring apparatus according to one embodiment of the invention.

FIG. 4 shows an example of functional blocks of a calculation system that forms the calculation device 60.

A processing section 110 performs various processes according to this embodiment based on a program (data) stored in an information storage medium 130. Specifically, a program that causes a computer to function as each section according to this embodiment (a program that causes a computer to execute the process of each section) is stored in the information storage medium 130.

The function of the processing section 110 may be implemented by hardware such as a processor (e.g., CPU or DSP) or ASIC (e.g., gate array) and a program.

The processing section 110 includes a carrier amplitude coefficient calculation section 52 and a matrix element calculation section 54.

A storage section 120 serves as a work area for the processing section and the like. The function of the storage section 120 may be implemented by a RAM or the like.

The information storage medium 130 (computer-readable medium) stores a program, data, and the like. The function of the information storage medium 130 may be implemented by an optical disk (CD or DVD), a magneto-optical disk (MO), a magnetic disk, a hard disk, a magnetic tape, a memory (ROM), or the like.

The principal axis direction of the optical element of the optical system 10 may be set and the operation of the light source 12 may be controlled based on a program stored in the information storage medium 130.

The calculation device 60 may have a function of controlling the operation of the measuring apparatus 1. Specifically, the calculation device 60 may set (change) the principal axis direction of the optical element by controlling driver/detection sections 70-1 to 70-4 described later, control the operation of the light source 12, and control the operations of the light intensity information acquisition section 40 and the calculation section 50.

1-5: Driver/Detection Section

The measuring apparatus 1 may further include the driver/detection sections 70-1 to 70-4. The driver section of the driver/detection section is an actuator that variably sets the principal axis direction of the optical element (polarizer 22, first carrier retarder 24, second carrier retarder 34, and analyzer 32) of the optical system. The detection section is a sensor that detects the principal axis direction of the optical element.

(2) Mueller Matrix Element Calculation Principle

The Mueller matrix element calculation principle employed in the measuring apparatus according to this embodiment is described below.

2-1: Theoretical Expression for Optical System 10

The Mueller matrices of the optical system 10 and the sample 100 are expressed as follows.

$$P_{\theta P} = \frac{1}{2}\begin{bmatrix} 1 & \cos 2\theta_P & \sin 2\theta_P & 0 \\ \cos 2\theta_P & \cos^2 2\theta_P & \cos 2\theta_P \sin 2\theta_P & 0 \\ \sin 2\theta_P & \sin 2\theta_P \cos 2\theta_P & \sin^2 2\theta_P & 0 \\ 0 & 0 & 0 & 0 \end{bmatrix} \quad (1)$$

$$P_{\theta A} = \frac{1}{2}\begin{bmatrix} 1 & \cos 2\theta_A & \sin 2\theta_A & 0 \\ \cos 2\theta_A & \cos^2 2\theta_A & \cos 2\theta_a \sin 2\theta_A & 0 \\ \sin 2\theta_A & \sin 2\theta_A \cos 2\theta_A & \sin^2 2\theta_A & 0 \\ 0 & 0 & 0 & 0 \end{bmatrix} \quad (2)$$

$$R_{\theta 1} = \begin{bmatrix} 1 & 0 & 0 & 0 \\ 0 & 1 - 2\sin^2(\phi_1(\sigma)/2)\sin^2 2\theta_1 & \sin^2(\phi_1(\sigma)/2)\sin 4\theta_1 & -\sin\phi_1(\sigma)\sin 2\theta_1 \\ 0 & \sin^2(\phi_1(\sigma)/2)\sin 4\theta_1 & 1 - 2\sin^2(\phi_1(\sigma)/2)\cos^2 2\theta_1 & \sin\phi_1(\sigma)\cos 2\theta_1 \\ 0 & \sin\phi_1(\sigma)\sin 2\theta_1 & -\sin\phi_1(\sigma)/2\cos 2\theta_1 & \cos\phi_1(\sigma) \end{bmatrix} \quad (3)$$

$$R_{\theta 2} = \begin{bmatrix} 1 & 0 & 0 & 0 \\ 0 & 1 - 2\sin^2(\phi_2(\sigma)/2)\sin^2 2\theta_2 & \sin^2(\phi_2(\sigma)/2)\sin 4\theta_2 & -\sin\phi_2(\sigma)\sin 2\theta_2 \\ 0 & \sin^2(\phi_2(\sigma)/2)\sin 4\theta_2 & 1 - 2\sin^2(\phi_2(\sigma)/2)\cos^2 2\theta_2 & \sin\phi_2(\sigma)\cos 2\theta_2 \\ 0 & \sin\phi_2(\sigma)\sin 2\theta_2 & -\sin\phi_2(\sigma)/2\cos 2\theta_2 & \cos\phi_2(\sigma) \end{bmatrix} \quad (4)$$

$$X = \begin{bmatrix} m_{00} & m_{01} & m_{02} & m_{03} \\ m_{10} & m_{11} & m_{12} & m_{13} \\ m_{20} & m_{21} & m_{22} & m_{23} \\ m_{30} & m_{31} & m_{32} & m_{33} \end{bmatrix} \quad (5)$$

$P_{\theta P}$ is the Mueller matrix of the polarizer 22, and $\theta_P$ is the principal axis direction of the polarizer 22. $P_{\theta A}$ is the Mueller matrix of the analyzer 32, and $\theta_A$ is the principal axis direction of the analyzer 32. $R_{\theta 1}$ is the Mueller matrix of the first carrier retarder 24. $\theta_1$ is the principal axis direction of the first carrier retarder 24, and $\phi_1(\sigma)$ is the retardation of the first carrier retarder 24. $R_{\theta 2}$ is the Mueller matrix of the second carrier retarder 34. $\theta_2$ is the principal axis direction of the second carrier retarder 34, and $\phi_2(\sigma)$ is the retardation of the second carrier retarder 34. X is the Mueller matrix of the sample 100.

The relationship between each Mueller matrix and the Stokes parameters is expressed as follows.

$$S_{out} = P_{\theta A} \cdot R_{\theta 2} \cdot X \cdot R_{\theta 1} \cdot P_{\theta P} \cdot S_{in} \quad (6)$$

$S_{out} = \{s_0, s_1, s_2, s_3\}^T = \{$light intensity, difference in light intensity between horizontal linearly polarized component and vertical linearly polarized component, difference in light intensity between 45° linearly polarized component and −45° linearly polarized component, difference in light intensity between clockwise circularly polarized component and counterclockwise circularly polarized component$\}^T$ indicates an exit Stokes parameter, and $S_{in} = \{P_0(\sigma), 0, 0, 0\}^T$ indicates an incident Stokes parameter. $P_0(\sigma)$ is the light intensity of the light source 12 with respect to the wave number.

The light intensity $P(\sigma)$ of the measurement light is given by the following theoretical expression by substituting the expressions (1) to (5), $S_{out}$, and $S_{in}$ in the expression (6).

$$P(\sigma) = N_{00}(\sigma) + N_{C0}(\sigma)\cos\phi_1(\sigma) + N_{S0}(\sigma)\sin\phi_1(\sigma) + \quad (7)$$
$$N_{0C}(\sigma)\cos\phi_2(\sigma) + N_{0S}(\sigma)\sin\phi_2(\sigma) +$$
$$N_{CC}(\sigma)\cos\phi_1(\sigma)\cos\phi_2(\sigma) + N_{SC}(\sigma)\sin\phi_1(\sigma)\cos\phi_2(\sigma) +$$
$$N_{CC}(\sigma)\cos\phi_1(\sigma)\sin\phi_2(\sigma) + N_{SS}(\sigma)\sin\phi_1(\sigma)\sin\phi_2(\sigma)$$

In the invention, the coefficients $N_{00}$ to $N_{SS}$ of the respective terms are referred to as carrier amplitude coefficients. As is clear from the expression (7), nine carrier amplitude coefficients $N_{00}$ to $N_{SS}$ appear in a theoretical expression for the light intensity $P(\sigma)$ of a measurement light. The nine carrier amplitude coefficients $N_{00}$ to $N_{SS}$ are generally given by the following theoretical expressions.

$$N_{00}(\sigma) = P_0(\sigma)\begin{bmatrix} A_{0000}m_{00}(\sigma) + A_{0001}m_{01}(\sigma) + A_{0002}m_{02}(\sigma) + \\ A_{0010}m_{10}(\sigma) + A_{0011}m_{11}(\sigma) + A_{0012}m_{12}(\sigma) + \\ A_{0020}m_{20}(\sigma) + A_{0021}m_{21}(\sigma) + A_{0022}m_{22}(\sigma) \end{bmatrix} \quad (8a)$$

$$N_{C0}(\sigma) = P_0(\sigma)\begin{bmatrix} A_{C001}m_{01}(\sigma) + A_{C002}m_{02}(\sigma) + A_{C011}m_{11}(\sigma) + \\ A_{C012}m_{12}(\sigma) + A_{C021}m_{21}(\sigma) + A_{C022}m_{22}(\sigma) \end{bmatrix} \quad (8b)$$

$$N_{S0}(\sigma) = P_0(\sigma)[A_{S003}m_{03}(\sigma) + A_{S013}m_{13}(\sigma) + A_{S023}m_{23}(\sigma)] \quad (8c)$$

-continued $$N_{0C}(\sigma) = P_0(\sigma)\begin{bmatrix} A_{0C10}m_{10}(\sigma) + A_{0C11}m_{11}(\sigma) + A_{0C12}m_{12}(\sigma) + \\ A_{0C20}m_{20}(\sigma) + A_{0C21}m_{21}(\sigma) + A_{0C22}m_{22}(\sigma) \end{bmatrix} \quad (8d)$$

$$N_{0S}(\sigma) = P_0(\sigma)[A_{0S30}m_{30}(\sigma) + A_{0S31}m_{31}(\sigma) + A_{0S32}m_{32}(\sigma)] \quad (8e)$$

$$N_{CC}(\sigma) = P_0(\sigma)\begin{bmatrix} A_{CC11}m_{11}(\sigma) + A_{CC12}m_{12}(\sigma) + \\ A_{CC21}m_{21}(\sigma) + A_{CC22}m_{22}(\sigma) \end{bmatrix} \quad (8f)$$

$$N_{SC}(\sigma) = P_0(\sigma)[A_{SC13}m_{13}(\sigma) + A_{SC23}m_{23}(\sigma)] \quad (8g)$$

$$N_{CS}(\sigma) = P_0(\sigma)[A_{CS31}m_{31}(\sigma) + A_{CS32}m_{32}(\sigma)] \quad (8h)$$

$$N_{SS}(\sigma) = P_0(\sigma)[A_{SS33}m_{33}(\sigma)] \quad (8i)$$

Specifically, nine proportional constants (carrier amplitude coefficients) that appear in the expression (7) are linear combinations of the Mueller matrix elements $m_{00}$ to $m_{33}$ of the sample 100.

The coefficients $A_{0000}$ to $A_{SS33}$ include principal axis direction information relating to the optical elements described later. Therefore, the theoretical expressions for the carrier amplitude coefficients shown by the expressions (8a) to (8i) include the principal axis direction information relating to the optical elements and at least one matrix element.

2-2: Calculating of Coefficients $A_{0000}$ to $A_{SS33}$

The coefficients $A_{0000}$ to $A_{SS33}$ that appear in the expressions (8a) to (8i) are given by the following expressions.

$$A_{0000} = 1 \quad (9a)$$

$$A_{0001} = \cos 2(\theta_1 - \theta_P)\cos 2\theta_1 \quad (9b)$$

$$A_{0002} = \cos 2(\theta_1 - \theta_P)\sin 2\theta_1 \quad (9c)$$

$$A_{0010} = \cos 2(\theta_4 - \theta_2)\cos 2\theta_2 \quad (9d)$$

$$A_{0011} = \cos 2(\theta_4 - \theta_2)\cos 2(\theta_1 - \theta_P)\cos 2\theta_1 \cos 2\theta_2 \quad (9e)$$

$$A_{0012} = \cos 2(\theta_4 - \theta_2)\cos 2(\theta_1 - \theta_P)\sin 2\theta_1 \cos 2\theta_2 \quad (9f)$$

$$A_{0020} = \cos 2(\theta_4 - \theta_2)\sin 2\theta_2 \quad (9g)$$

$$A_{0021} = \cos 2(\theta_4 - \theta_2)\cos 2(\theta_1 - \theta_P)\cos 2\theta_1 \sin 2\theta_2 \quad (9h)$$

$$A_{0022} = \cos 2(\theta_4 - \theta_2)\cos 2(\theta_1 - \theta_P)\sin 2\theta_1 \sin 2\theta_2 \quad (9i)$$

$$A_{C001} = \sin 2(\theta_1 - \theta_P)\sin 2\theta_1 \quad (10a)$$

$$A_{C002} = -\sin 2(\theta_1 - \theta_P)\cos 2\theta_1 \quad (10b)$$

$$A_{C011} = -\sin 2(\theta_1 - \theta_P)\cos 2(\theta_4 - \theta_2)\sin 2\theta_1 \cos 2\theta_2 \quad (10c)$$

$$A_{C012} = -\sin 2(\theta_1 - \theta_P)\cos 2(\theta_4 - \theta_2)\cos 2\theta_1 \cos 2\theta_2 \quad (10d)$$

$$A_{C021} = \sin 2(\theta_1 - \theta_P)\cos 2(\theta_4 - \theta_2)\sin 2\theta_1 \sin 2\theta_2 \quad (10e)$$

$$A_{C022} = -\sin 2(\theta_1 - \theta_P)\cos 2(\theta_4 - \theta_2)\cos 2\theta_1 \sin 2\theta_2 \quad (10f)$$

$$A_{S003} = \sin 2(\theta_1 - \theta_P) \quad (11a)$$

$$A_{S013} = \sin 2(\theta_1 - \theta_P)\cos 2(\theta_4 - \theta_2)\cos 2\theta_2 \quad (11b)$$

$$A_{S023} = \sin 2(\theta_1 - \theta_P)\cos 2(\theta_4 - \theta_2)\sin 2\theta_2 \quad (11c)$$

$$A_{0C10} = -\sin 2(\theta_4 - \theta_2)\sin 2\theta_2 \quad (12a)$$

$$A_{0C11} = -\sin 2(\theta_4 - \theta_2)\cos 2(\theta_1 - \theta_P)\cos 2\theta_1 \sin 2\theta_2 \quad (12b)$$

$$A_{0C12} = -\sin 2(\theta_4 - \theta_2)\cos 2(\theta_1 - \theta_P)\sin 2\theta_1 \sin 2\theta_2 \quad (12c)$$

$$A_{0C20} = \sin 2(\theta_4 - \theta_2)\cos 2\theta_2 \quad (12d)$$

$$A_{0C21} = \sin 2(\theta_4 - \theta_2)\cos 2(\theta_1 - \theta_P)\cos 2\theta_1 \cos 2\theta_2 \quad (12e)$$

$$A_{0C22} = \sin 2(\theta_4 - \theta_2)\cos 2(\theta_1 - \theta_P)\sin 2\theta_1 \cos 2\theta_2 \quad (12f)$$

$$A_{0S30} = \sin 2(\theta_4 - \theta_2) \quad (13a)$$

$$A_{0S31} = \sin 2(\theta_4 - \theta_2)\cos 2(\theta_1 - \theta_P)\cos 2\theta_1 \quad (13b)$$

$$A_{0S32} = \sin 2(\theta_4 - \theta_2)\cos 2(\theta_1 - \theta_P)\sin 2\theta_1 \quad (13c)$$

$$A_{CC11} = -\sin 2(\theta_1 - \theta_P)\sin 2(\theta_4 - \theta_2)\sin 2\theta_1 \sin 2\theta_2 \quad (14a)$$

$$A_{CC12} = \sin 2(\theta_1 - \theta_P)\sin 2(\theta_4 - \theta_2)\cos 2\theta_1 \sin 2\theta_2 \quad (14b)$$

$$A_{CC21} = \sin 2(\theta_1 - \theta_P)\sin 2(\theta_4 - \theta_2)\sin 2\theta_1 \cos 2\theta_2 \quad (14c)$$

$$A_{CC22} = -\sin 2(\theta_1 - \theta_P)\sin 2(\theta_4 - \theta_2)\cos 2\theta_1 \cos 2\theta_2 \quad (14d)$$

$$A_{SC13} = -\sin 2(\theta_1 - \theta_P)\sin 2(\theta_4 - \theta_2)\sin 2\theta_2 \quad (15a)$$

$$A_{SC23} = \sin 2(\theta_1 - \theta_P)\sin 2(\theta_4 - \theta_2)\cos 2\theta_2 \quad (15b)$$

$$A_{CS31} = \sin 2(\theta_1 - \theta_P)\sin 2(\theta_4 - \theta_2)\sin 2\theta_1 \quad (16a)$$

$$A_{CS32} = -\sin 2(\theta_1 - \theta_P)\sin 2(\theta_4 - \theta_2)\cos 2\theta_1 \quad (16b)$$

$$A_{SS33} = \sin 2(\theta_1 - \theta_P)\sin 2(\theta_4 - \theta_2) \quad (17)$$

Specifically, the coefficients $A_{0000}$ to $A_{SS33}$ can be obtained as numerical values by substituting the principal axis direction information ($\theta_P, \theta_1, \theta_2, \theta_4$) relating to the optical element in the expressions (9a) to (17).

2-3: Calculation of Carrier Amplitude Coefficients $N_{00}$ to $N_{SS}$

The carrier amplitude coefficients $N_{00}$ to $N_{SS}$ can be calculated utilizing the correlation function. A method of calculating the carrier amplitude coefficients $N_{00}$ to $N_{SS}$ is described below.

When the carrier amplitude coefficients $N_{00}$ to $N_{SS}$ are written as follows, $$N_0(\sigma) = N_{00}(\sigma) \quad (18a)$$

$$N_1(\sigma) = N_{C0}(\sigma) + iN_{S0}(\sigma) \quad (18b)$$

$$N_2(\sigma) = N_{0C}(\sigma) + iN_{0S}(\sigma) \quad (18c)$$

$$N_-(\sigma) = \frac{1}{2}[N_{CC}(\sigma) + N_{SS}(\sigma)] + i\frac{1}{2}[-N_{SC}(\sigma) + N_{CS}(\sigma)] \quad (18d)$$

$$N_+(\sigma) = \frac{1}{2}[N_{CC}(\sigma) - N_{SS}(\sigma)] + i\frac{1}{2}[N_{SC}(\sigma) + N_{CS}(\sigma)] \quad (18e)$$

the expression (7) is written as follows.

$$P(\sigma) = N_0(\sigma) + |N_1(\sigma)|\cos[\phi_1(\sigma) - \arg N_1(\sigma)] + \quad (19)$$
$$|N_2(\sigma)|\cos[\phi_2(\sigma) - \arg N_2(\sigma)] +$$
$$|N_-(\sigma)|\cos[\phi_2(\sigma) - \phi_1(\sigma) - \arg N_-(\sigma)] +$$
$$|N_+(\sigma)|\cos[\phi_2(\sigma) + \phi_1(\sigma) - \arg N_+(\sigma)]$$

where, arg is an operator that has an argument, and i is an imaginary unit.

The first carrier retarder 24 and the second carrier retarder 34 are elements that change the retardation between linearly polarized components that perpendicularly intersect before and after passing through the elements. The change in phase difference is referred to as retardation. The retardation of a carrier retarder formed of a birefringent medium changes as shown by the following expression with respect to the wave number σ.

$$\phi_j(\sigma) = 2\pi D_j B(\sigma)\sigma = 2\pi L_j \sigma + \Phi_j(\sigma) \tag{20}$$

where, $$L_j = \frac{1}{2\pi} \frac{d\phi_j}{d\sigma}\bigg|_{\sigma_0} = D_j\left(B(\sigma_0) + \frac{dB}{d\sigma}\bigg|_{\sigma_0} \sigma_0\right) \tag{21a}$$

$$\Phi_j(\sigma) = \{\phi_j(\sigma_0) - 2\pi L_j \sigma_0\} + \frac{1}{2}\frac{d^2\phi_j}{d\sigma^2}\bigg|_{\sigma_0} (\sigma-\sigma_0)^2 + \ldots \tag{21b}$$

$\phi_j(\sigma)$ is the retardation of the carrier retarder. $D_j$ is the thickness of the carrier retarder, and $B(\sigma)$ is the birefringence of the carrier retarder. $\sigma_0$ is the center wave number of the measurement light.

The second equation in the expression (20) means that the retardation $\phi_j(\sigma)$ of the carrier retarder can be expanded in the form of the sum of the term $2\pi L_j \sigma$ that changes linearly with respect to the wave number σ and the term $\Phi_j(\sigma)$ that changes nonlinearly with respect to the wave number σ. Specifically, the first term is a term proportional to σ, and the second term is a portion obtained by removing the term proportional to σ from the retardation. If the dispersion (i.e., the change rate with respect to the wave number) of $B(\sigma)$ is not too large, the nonlinear term $\Phi_j(\sigma)$ decreases. Therefore, $\phi_j(\sigma)$ increases almost linearly with respect to the wave number σ, as is clear from the expression (20).

Substituting the expression (20) in the expression (19) yields the following expression.

$$P(\sigma) = N_0(\sigma) + |N_1(\sigma)|\cos[2\pi L_1 \sigma + \Phi_1(\sigma) - \arg N_1(\sigma)] + \tag{22}$$

$$|N_2(\sigma)|\cos[2\pi L_2 \sigma + \Phi_2(\sigma) - \arg N_2(\sigma)] +$$

$$|N_-(\sigma)|\cos\left[\begin{array}{c}2\pi(L_2-L_1)\sigma + \Phi_2(\sigma) - \\ \Phi_1(\sigma) - \arg N_-(\sigma)\end{array}\right] +$$

$$|N_+(\sigma)|\cos\left[\begin{array}{c}2\pi(L_2+L_1)\sigma + \Phi_2(\sigma) + \\ \Phi_1(\sigma) - \arg N_+(\sigma)\end{array}\right]$$

Since the retardations $\phi_1(\sigma)$ and $\phi_2(\sigma)$ of the carrier retarder change almost proportionally to the wave number σ, the first term on the right side of the expression (22) is a component that gradually changes with respect to the wave number, and the remaining terms are components that vibrate in a pseudo sine wave manner in center cycles $1/L_1$, $1/L_2$, $1/(L_2-L_1)$, and $1/(L_2+L_1)$, respectively. Therefore, $N_0(\sigma)$ to $N_+(\sigma)$ can be independently determined by separating each component on the right side of the expression (22) utilizing frequency filtering and demodulating the amplitude and the phase of each term.

The separation/demodulation means for each term is not particularly limited. For example, the separation/demodulation means may be implemented by applying Fourier transform. A specific method is given below.

Figure 5:
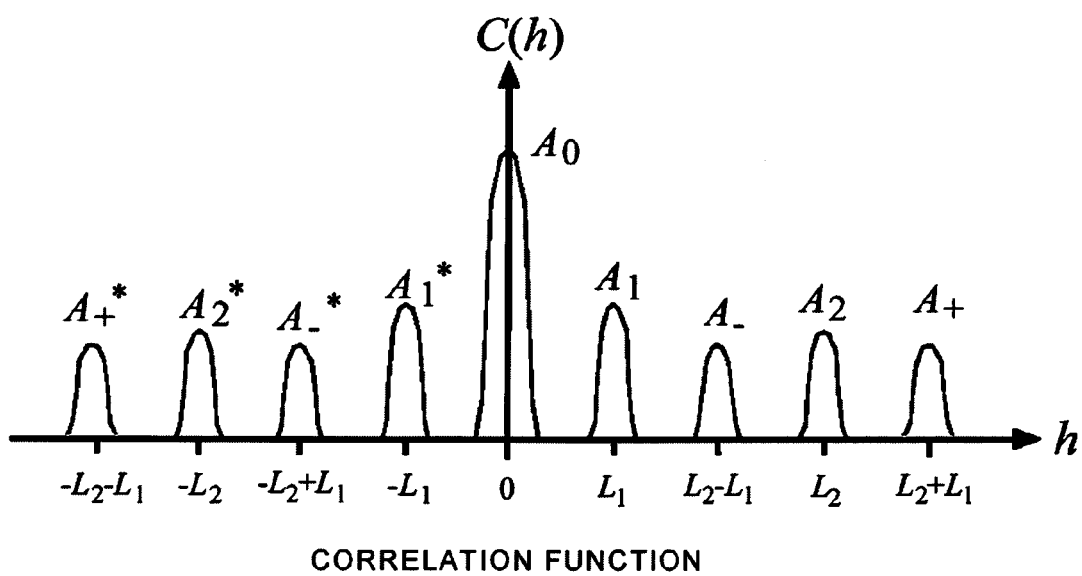
FIG. 5 is a diagram illustrative of the measurement principle according to the invention.

The light intensity $P(\sigma)$ of the measurement light is subjected to inverse Fourier transform using FFT. The correlation function of the measurement light is obtained by this process, as derived from the expression (22).

$$C(h) = A_0(h) + A_1(h-L_1) + A_1^*(-h-L_1) + \tag{23}$$
$$A_2(h-L_2) + A_2^*(-h-L_2) +$$
$$A_-(h-[L_2-L_1]) + A_-^*(-h-[L_2-L_1]) +$$
$$A_+(h-[L_2+L_1]) + A_+^*(-h-[L_2+L_1])$$

where, $$A_0(h) = F^{-1}\{N_0(\sigma)\} \tag{24a}$$

$$A_1(h) = F^{-1}\{N_1(\sigma)\exp i[\Phi_1(\sigma)]\} \tag{24b}$$

$$A_2(h) = F^{-1}\{N_2(\sigma)\exp i[\Phi_2(\sigma)]\} \tag{24c}$$

$$A_-(h) = F^{-1}\{N_-(\sigma)\exp i[\Phi_2(\sigma)-\Phi_1(\sigma)]\} \tag{24d}$$

$$A_+(h) = F^{-1}\{N_+(\sigma)\exp i[\Phi_2(\sigma)+\Phi_1(\sigma)]\} \tag{24e}$$

and * is a complex conjugate. As shown in FIG. 5, the correlation function $C(h)$ includes nine components around the reciprocals $0, \pm L_1, \pm L_2, \pm(L_2-L_1)$, and $\pm(L_2+L_1)$ of the cycles of the respective vibrational components. The components included in the correlation function $C(h)$ can be separated on the h-axis by appropriately selecting the reciprocals of these cycles. Subjecting five components around $h=0, L_1, L_2, (L_2-L_1)$, and $(L_2+L_1)$ to Fourier transform yields the following expressions.

$$F[A_0(h)]=N_0(\sigma) \tag{25a}$$

$$F[A_1(h-L_1)]=N_1(\sigma)\exp i[\phi_1(\sigma)] \tag{25b}$$

$$F[A_2(h-L_2)]=N_2(\sigma)\exp i[\phi_2(\sigma)] \tag{25c}$$

$$F[A_-(h-[L_2-L_1])]=N_-(\sigma)\exp i[\phi_2(\sigma)-\phi_1(\sigma)] \tag{25d}$$

$$F[A_+(h-[L_2+L_1])]=N_+(\sigma)\exp i[\phi_2(\sigma)+\phi_1(\sigma)] \tag{25e}$$

$\phi_1(\sigma)$ and $\phi_2(\sigma)$ on the right side of each expression indicate the retardations of the first carrier retarder 24 and the second carrier retarder 34. These parameters are parameters of the optical system 10 regardless of the sample 100, and can be calculated in advance. Therefore, $N_0(\sigma)$ to $N_+(\sigma)$ defined by the expressions (18a) to (18e) are calculated as follows by dividing the above expressions by these parameters.

$$N_0(\sigma) = F[A_0(h)] \tag{26a}$$

$$N_1(\sigma) = \frac{F[A_1(h-L_1)]}{\exp i[\phi_1(\sigma)]} \tag{26b}$$

$$N_2(\sigma) = \frac{F[A_2(h-L_2)]}{\exp i[\phi_2(\sigma)]} \tag{26c}$$

$$N_-(\sigma) = \frac{F[A_-(h-[L_2-L_1])]}{\exp i[\phi_2(\sigma)-\phi_1(\sigma)]} \tag{26d}$$

$$N_+(\sigma) = \frac{F[A_+(h-[L_2+L_1])]}{\exp i[\phi_2(\sigma)+\phi_1(\sigma)]} \tag{26e}$$

The carrier amplitude coefficients $N_{00}(\sigma)$ to $N_{SS}(\sigma)$ are given by the following expressions from the expressions (18a) to (18e).

$$N_{00}(\sigma)=N_0(\sigma) \tag{27a}$$

$$N_{C0}(\sigma)=Re[N_1(\sigma)] \tag{27b}$$

$$N_{S0}(\sigma)=Im[N_1(\sigma)] \tag{27c}$$

$$N_{0C}(\sigma)=Re[N_2(\sigma)] \quad (27d)$$

$$N_{0S}(\sigma)=Im[N_2(\sigma)] \quad (27e)$$

$$N_{CC}(\sigma)=Re[N_-(\sigma)+N_+(\sigma)] \quad (27f)$$

$$N_{SC}(\sigma)=Im[-N_-(\sigma)+N_+(\sigma)] \quad (27g)$$

$$N_{CS}(\sigma)=Im[N_-(\sigma)+N_+(\sigma)] \quad (27h)$$

$$N_{SS}(\sigma)=Re[N_-(\sigma)-N_+(\sigma)] \quad (27i)$$

Re and Im are operators respectively indicating the real part and the imaginary part.

The real parts and the imaginary parts of $N_0(\sigma)$ and $N_1(\sigma)$ to $N_+(\sigma)$ that appear in the expressions (26a) to (26e) can be calculated by utilizing the correlation function of the measurement light. Therefore, the carrier amplitude coefficients $N_{00}(\sigma)$ to $N_{SS}(\sigma)$ can be calculated by utilizing the resulting values.

2-4: Calculation of Mueller Matrix Elements

As is clear from the expressions (8a) to (8i), the nine carrier amplitude coefficients $N_{00}$ to $N_{SS}$ have a form in which the linear combination of the Mueller matrix elements of the sample 100 is multiplied by the light intensity $P_0(\sigma)$ of the light source 12. The light intensity $P_0$ of the light source, the coefficients $A_{0000}$ to $A_{SS33}$, and the carrier amplitude coefficients $N_{00}$ to $N_{SS}$ can be calculated as numerical values. Specifically, the expressions (8a) to (8i) include the sixteen Mueller matrix elements $m_{00}$ to $m_{33}$ as unknown quantities. Therefore, the Mueller matrix elements can be calculated by solving these expressions.

As indicated by the expressions (8a) to (8i), the nine relational expressions include sixteen unknown quantities. Therefore, it is impossible to calculate all of the sixteen Mueller matrix elements from only the nine relational expressions.

Specifically, if sixteen appropriate expressions that indicate the relationship among the Mueller matrix elements can be derived, all of the sixteen Mueller matrix elements can be calculated by solving these expressions.

The coefficients $A_{0000}$ to $A_{SS33}$ that appear in the expressions (8a) to (8i) are values calculated by using the principal axis directions $\theta_P$, $\theta_1$, $\theta_2$, and $\theta_A$ of the four optical elements. The carrier amplitude coefficients $N_{00}$ to $N_{SS}$ are values calculated from the light intensity information relating to the measurement light. Specifically, nine expressions that indicate the relationship among the sixteen matrix elements $m_{00}$ to $m_{33}$ can be derived based on the light intensity information relating to the measurement light and the principal axis directions of the optical elements. Nine relational expressions including the sixteen Mueller matrix elements can be derived from the optical system 10 by changing setting of the principal axis direction of the polarizer 22, the first carrier retarder 24, the second carrier retarder 34, and the analyzer 32.

Therefore, the number of expressions that indicate the relationship among the sixteen Mueller matrix elements $m_{00}$ to $m_{33}$ can be increased by utilizing the light intensity information relating to a plurality of measurement lights modulated by the sample 100 and the optical system 10 that differ in the principal axis directions of the polarizer 22, the first carrier retarder 24, the second carrier retarder 34, and the analyzer 32 and the theoretical expression for the respective measurement light.

All of the sixteen Mueller matrix elements can be calculated by selecting appropriate relational expressions that indicate the relationship among the sixteen Mueller matrix elements and simultaneously solving the relational expressions.

Figure 6:
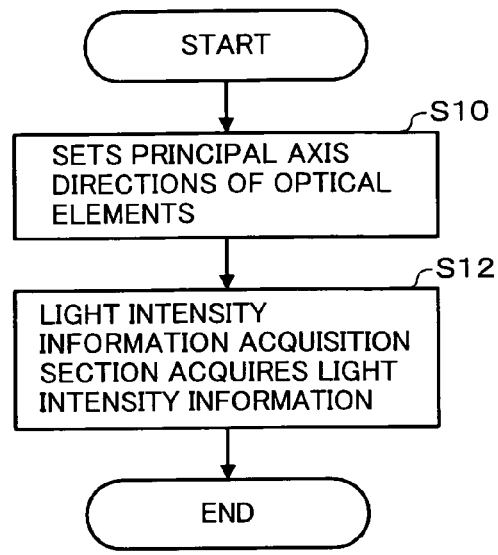
FIG. 6 is a flowchart illustrative of a light intensity information acquisition process.
Figure 7:
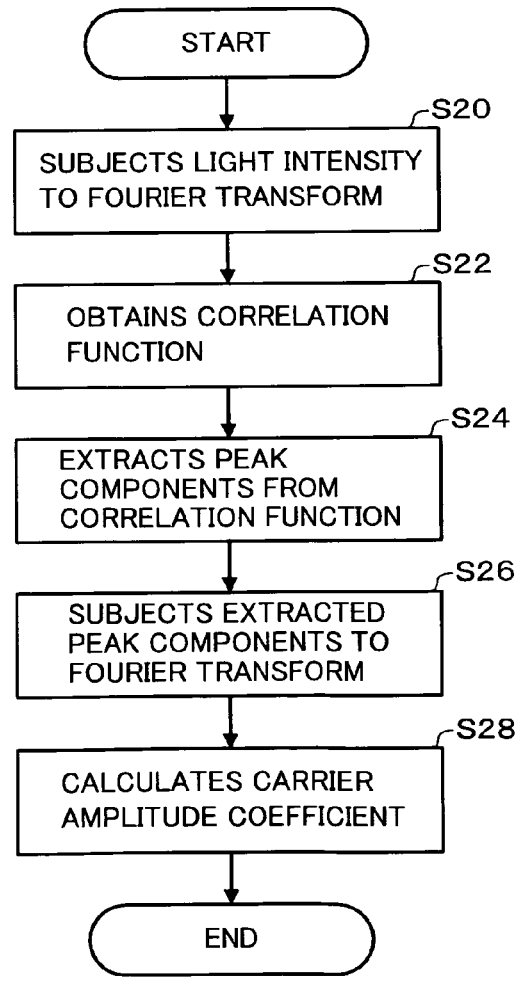
FIG. 7 is a flowchart illustrative of a carrier amplitude coefficient calculation process.
Figure 8:
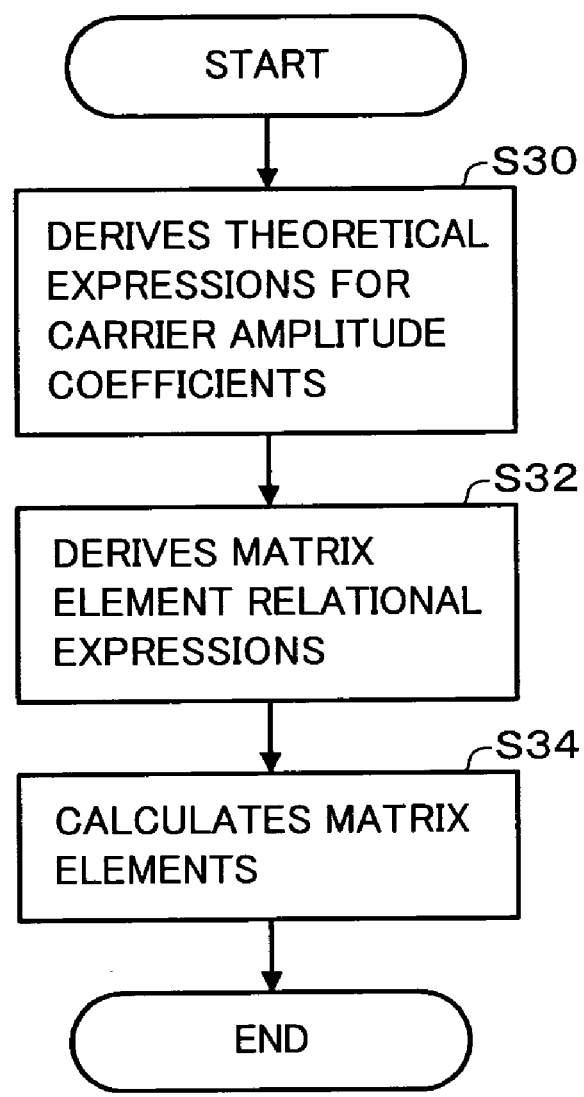
FIG. 8 is a flowchart illustrative of a matrix element calculation process.

(3) Mueller Matrix Element Calculation Process Performed by Measuring Apparatus According to this Embodiment FIGS. 6 to 8 are flowcharts showing the operation of the measuring apparatus according to this embodiment.

3-1: Light Intensity Information Acquisition Process

FIG. 6 is a flowchart showing the light intensity information acquisition process.

The principal axis directions of the optical elements (polarizer 22, first carrier retarder 24, second carrier retarder 34, and analyzer 32) of the optical system 10 are set (step S10).

Light is then emitted from the light source 12, and the measurement light modulated by the optical elements included in the optical system 10 and the sample 100 is received by the light-receiving section 14. The light intensity information acquisition section 40 acquires the light intensity information relating to the measurement light (step S12). The light intensity information may be acquired as the light intensity $P(\sigma)$, as shown in FIG. 3A.

A step of providing the sample 100 in the optical path L of the optical system 10 may be performed before the step S12. This step may be performed before or after the step of setting the principal axis directions of the optical elements.

In the light intensity information acquisition process, the light intensity information acquisition section 40 acquires the light intensity information relating to a plurality of measurement lights. The plurality of measurement lights are obtained from the optical system 10 by changing setting of the principal axis direction of at least one of the optical elements (polarizer 22, first carrier retarder 24, second carrier retarder 34, and analyzer 32). In the light intensity information acquisition process, the steps S10 and S12 are repeated a number of times while changing the principal axis direction of at least one of the four optical elements.

In the light intensity information acquisition process, first light intensity information is acquired by setting the principal axis directions of the optical elements to a first condition. Second light intensity information is then acquired by setting (changing) the principal axis directions of the optical elements to a second condition. The above operation is repeated to obtain M pieces of light intensity information.

In the invention, the principal axis direction information relating to the optical elements and the light intensity information relating to a plurality of measurement lights acquired by the light intensity information acquisition section 40 are stored in the storage device 55. The storage device 55 stores the light intensity information relating to the measurement lights and the principal axis direction information relating to the optical elements while associating the light intensity information with the principal axis direction information. Specifically, the storage device 55 stores the first light intensity information to the Mth light intensity information corresponding to the first principal axis direction information to the Mth principal axis direction information, respectively.

3-2: Carrier Amplitude Coefficient Calculation Process

FIG. 7 is a flowchart showing the carrier amplitude coefficient calculation process. In the carrier amplitude coefficient calculation process, the calculation section 50 calculates the carrier amplitude coefficient based on the light intensity information acquired by the light intensity information acquisition section 40. Although the following description is given taking a Fourier transform process as an example, the invention is not limited thereto.

The light intensity $P(\sigma)$ acquired by the light intensity information acquisition section 40 is subjected to Fourier transform using the wave number $\sigma$ (step S20) to obtain a correlation function (step S22).

Since the correlation function includes peak components (see FIG. 3B or 5), the correlation function is filtered to extract the peak components (step S24).

The extracted peak components are subjected to Fourier transform (step S26). The values of the real part and the imaginary part of each peak component are thus acquired as the measured values.

At least one carrier amplitude coefficient is calculated based on the values of the real part and the imaginary part of each spectral peak, as indicated by the expressions (27a) to (27i) (step S28).

The measuring apparatus according to this embodiment performs the processes in the steps S20 to S28 on each of a plurality of pieces of light intensity information (first light intensity information to Mth light intensity information) acquired by the intensity information acquisition section 40. Specifically, the measuring apparatus according to this embodiment calculates the carrier amplitude coefficient of each light intensity information.

The measuring apparatus 1 may store the carrier amplitude coefficient obtained from a plurality of pieces of light intensity information in the storage device 55 corresponding to the principal axis direction information relating to the optical elements of the optical system 10.

3-3: Mueller Matrix Element Calculation Process

FIG. 8 is a flowchart showing the Mueller matrix element calculation process. In the Mueller matrix element calculation process, the calculation section 50 calculates the Mueller matrix elements based on the carrier amplitude coefficients and the theoretical expressions for the carrier amplitude coefficients.

First, the theoretical expressions for the carrier amplitude coefficients are derived (step S30).

The coefficients of the theoretical expressions for the carrier amplitude coefficients change depending on the principal axis directions of the optical elements of the optical system 10, as described above. Therefore, the theoretical expressions for the carrier amplitude coefficients can be derived utilizing the principal axis direction information relating to the optical elements. The step of deriving the theoretical expressions for the carrier amplitude coefficients (step S30) may be performed at an arbitrary stage. For example, the step of deriving the theoretical expressions for the carrier amplitude coefficients may be performed when setting the principal axis directions of the optical system 10. The derived theoretical expressions (the first to the Mth theoretical expressions) are stored in the storage device 55.

A plurality of relational expressions that indicate the relationship among the sixteen Mueller matrix elements are derived by associating data relating to each carrier amplitude coefficient with the theoretical expression for the carrier amplitude coefficient (step S32).

The sixteen Mueller matrix elements are calculated by solving the relational expressions (step S34).

(4) Specific Mueller Matrix Element Calculation Example Using Measuring Apparatus According to this Embodiment The Mueller matrix element calculation process is described below while setting the principal axis directions of the optical elements (polarizer 22, first carrier retarder 24, second carrier retarder 34, and analyzer 32) of the optical system 10.

The principal axis directions of the polarizer 22, the first carrier retarder 24, the second carrier retarder 34, and the analyzer 32 of the optical system 10 are set at 45°, 0°, 0°, and 45°. In this case, the carrier amplitude coefficients are expressed as follows.

$$N_{00}(\sigma)=P_0(\sigma)m_{00}(\sigma) \quad (28a)$$

$$N_{C0}(\sigma)=P_0(\sigma)m_{02}(\sigma) \quad (28b)$$

$$N_{S0}(\sigma)=-P_0(\sigma)m_{03}(\sigma) \quad (28c)$$

$$N_{0C}(\sigma)=P_0(\sigma)m_{20}(\sigma) \quad (28d)$$

$$N_{0S}(\sigma)=P_0(\sigma)m_{30}(\sigma) \quad (28e)$$

$$N_{CC}(\sigma)=P_0(\sigma)m_{22}(\sigma) \quad (28f)$$

$$N_{SC}(\sigma)=-P_0(\sigma)m_{23}(\sigma) \quad (28g)$$

$$N_{CS}(\sigma)=P_0(\sigma)m_{32}(\sigma) \quad (28h)$$

$$N_{SS}(\sigma)=-P_0(\sigma)m_{33}(\sigma) \quad (28i)$$

The principal axis directions of the optical elements of the optical system 10 are then set at 0°, 0°, 0°, and 45°. In this case, the carrier amplitude coefficients are expressed as follows.

$$N_{00}(\sigma)=P_0(\sigma)[m_{00}(\sigma)+m_{01}(\sigma)] \quad (29a)$$

$$N_{C0}(\sigma)=0 \quad (29b)$$

$$N_{S0}(\sigma)=0 \quad (29c)$$

$$N_{0C}(\sigma)=P_0(\sigma)[m_{20}(\sigma)+m_{21}(\sigma)] \quad (29d)$$

$$N_{0S}(\sigma)=P_0(\sigma)[m_{30}(\sigma)+m_{31}(\sigma)] \quad (29e)$$

$$N_{CC}(\sigma)=0 \quad (29f)$$

$$N_{SC}(\sigma)=0 \quad (29g)$$

$$N_{CS}(\sigma)=0 \quad (29h)$$

$$N_{SS}(\sigma)=0 \quad (29i)$$

The principal axis directions of the optical elements of the optical system 10 are then set at 45°, 0°, 0°, and 0°. In this case, the carrier amplitude coefficients are expressed as follows.

$$N_{00}(\sigma)=P_0(\sigma)[m_{00}(\sigma)+m_{10}(\sigma)] \quad (30a)$$

$$N_{C0}(\sigma)=P_0(\sigma)[m_{02}(\sigma)+m_{12}(\sigma)] \quad (30b)$$

$$N_{S0}(\sigma)=-P_0(\sigma)[m_{03}(\sigma)+m_{13}(\sigma)] \quad (30c)$$

$$N_{0C}(\sigma)=0 \quad (30d)$$

$$N_{0S}(\sigma)=0 \quad (30e)$$

$$N_{CC}(\sigma)=0 \quad (30f)$$

$$N_{SC}(\sigma)=0 \quad (30g)$$

$$N_{CS}(\sigma)=0 \quad (30h)$$

$$N_{SS}(\sigma)=0 \quad (30i)$$

The principal axis directions of the optical elements of the optical system 10 are then set at 0°, 0°, 0°, and 0°. In this case, the carrier amplitude coefficients are expressed as follows.

$$N_{00}(\sigma)=P_0(\sigma)[m_{00}(\sigma)+m_{01}(\sigma)+m_{10}(\sigma)+m_{11}(\sigma)] \quad (31a)$$

$$N_{C0}(\sigma)=0 \quad (31b)$$

$$N_{S0}(\sigma)=0 \quad (31c)$$

$$N_{0C}(\sigma)=0 \quad (31d)$$

$$N_{OS}(\sigma)=0 \quad (31\text{e})$$

$$N_{CC}(\sigma)=0 \quad (31\text{f})$$

$$N_{SC}(\sigma)=0 \quad (31\text{g})$$

$$N_{CS}(\sigma)=0 \quad (31\text{h})$$

$$N_{SS}(\sigma)=0 \quad (31\text{i})$$

The left side of each of the expressions (28a) to (31i) can be detected from the measured data, and the light intensity $P_0(\sigma)$ of the light source 12 can be determined in advance. Therefore, all of the sixteen Mueller matrix elements can be calculated by simultaneously solving these expressions.

Specifically, the measuring apparatus according to this embodiment can easily and quickly calculate the sixteen Mueller matrix elements utilizing a simple device.

According to the above-described example, all of the sixteen Mueller matrix elements can be calculated based only on the information obtained by the four light intensity information acquisition processes. Specifically, the sixteen Mueller matrix elements can be calculated based only on the four pieces of light intensity information by adjusting the principal axis directions of the optical elements. In other words, the sixteen Mueller matrix elements can be calculated based only on the first light intensity information to the fourth light intensity information obtained from the optical system 10 set to the first to fourth principal axis direction conditions.

Specifically, the sixteen Mueller matrix elements can be calculated by utilizing the four pieces of light intensity information obtained from the optical system 10 set to the four principal axis direction conditions including the first and second principal axis direction conditions that differ in the principal axis direction of at least one of the polarizer 22 and the first carrier retarder 24 and the third and fourth principal axis direction conditions that differ in the principal axis direction of at least one of the second carrier retarder 34 and the analyzer 32.

In other words, the sixteen Mueller matrix elements can be calculated based only on the four pieces of light intensity information obtained from the optical system 10 set to the four principal axis direction conditions including two principal axis direction conditions that differ in the principal axis direction of at least one of the polarizer 22 and the first carrier retarder 24 and another two principal axis direction conditions that differ in the principal axis direction of at least one of the second carrier retarder 34 and the analyzer 32.

This enables the Mueller matrix elements to be calculated using a small amount of data, whereby the Mueller matrix elements can be efficiently calculated.

In this specific example, the principal axis direction of each optical element is a multiple of 45°. Note that the invention is not limited thereto. The processing load of the measuring apparatus 1 can be reduced by appropriately setting the principal axis direction of each optical element.

For example, the principal axis directions of the optical elements (polarizer 22, first carrier retarder 24, second carrier retarder 34, and analyzer 32) of the optical system 10 may be set so that the angular difference in the principal axis direction is a multiple of 45°.

The principal axis directions of the polarizer 22 and the first carrier retarder 24 may be set so that the angular difference in the principal axis direction is constant. The principal axis directions of the second carrier retarder 34 and the analyzer 32 may be set so that the angular difference in the principal axis direction is constant.

When the optical element satisfies these above relationships, the calculation expressions can be simplified. Therefore, the processing load of the measuring apparatus 1 can be reduced.

In this specific example, the principal axis directions of the first carrier retarder 24 and the second carrier retarder 34 are fixed, and the principal axis directions of only the polarizer 22 and the analyzer 32 are changed. Note that the principal axis directions of the measuring apparatus according to this embodiment may be set in another way. For example, the principal axis directions of the polarizer 22 and the analyzer 32 may be fixed, and the principal axis directions of the first carrier retarder 24 and the second carrier retarder 34 may be changed. In the measuring apparatus according to this embodiment, the light intensity information acquisition section 40 may acquire the light intensity information relating to a plurality of measurement lights modulated by the optical system 10 in which setting of the principal axis direction of at least one of the polarizer 22 and the first carrier retarder 24 is changed, and acquire the light intensity information relating to a plurality of measurement lights modulated by the optical system 10 in which setting of the principal axis direction of at least one of the analyzer 32 and the second carrier retarder 34 is changed. This enables the expressions required to calculate the sixteen Mueller matrix elements to be derived.

(5) Industrial Applicability

As described above, the measuring apparatus according to this embodiment can easily, conveniently, and quickly calculate the sixteen matrix elements of the Mueller matrix that indicates the optical characteristics of the sample 100 (i.e., measurement target).

Various optical characteristics of the sample 100 can be determined by calculating all of the sixteen matrix elements of the Mueller matrix that indicates the optical characteristics of the sample 100 (i.e., measurement target). Specific examples of the optical characteristics are given below.

5-1: Depolarization

When a Mueller matrix $M(\sigma)$ is expressed as follows, $$M(\sigma) = \begin{bmatrix} m_{00}(\sigma) & m_{01}(\sigma) & m_{02}(\sigma) & m_{03}(\sigma) \\ m_{10}(\sigma) & m_{11}(\sigma) & m_{12}(\sigma) & m_{13}(\sigma) \\ m_{20}(\sigma) & m_{21}(\sigma) & m_{22}(\sigma) & m_{23}(\sigma) \\ m_{30}(\sigma) & m_{31}(\sigma) & m_{32}(\sigma) & m_{33}(\sigma) \end{bmatrix} \quad (32)$$

the depolarization of the sample 100 is expressed as follows.

$$Dep(M(\sigma)) = 1 - \frac{\sqrt{\left(\sum_{i,j} m_{i,j}^2(\sigma)\right) - m_{00}^2(\sigma)}}{\sqrt{3}\, m_{00}(\sigma)} \quad (33)$$

As is clear from the expression (33), all of the sixteen matrix elements of the Mueller matrix are necessary for calculating the depolarization. Specifically, the depolarization of the sample 100 can be easily and quickly calculated utilizing the measuring apparatus according to this embodiment.

5-2: Retardation, Principal Axis Direction, and Dichroism

The Mueller matrix of a sample having retardation, a principal axis direction, and dichroism is expressed as follows, $$M(\sigma) = \begin{bmatrix} P_f(\sigma)^2 + P_s(\sigma)^2 & A(\sigma)C & A(\sigma)S & 0 \\ A(\sigma)C & (P_f(\sigma)^2 + P_s(\sigma)^2)C^2 + S^2 B(\sigma)\cos\Delta(\sigma) & CS\left(\dfrac{P_f(\sigma)^2 + P_s(\sigma)^2 -}{B(\sigma)\cos\Delta(\sigma)}\right) & -B(\sigma)S\sin\Delta(\sigma) \\ A(\sigma)S & CS\left(\dfrac{P_f(\sigma)^2 + P_s(\sigma)^2 -}{B(\sigma)\cos\Delta(\sigma)}\right) & \left(\dfrac{P_f(\sigma)^2 + P_s(\sigma)^2 S^2 +}{C^2 B(\sigma)\cos\Delta(\sigma)}\right) & B(\sigma)C\sin\Delta(\sigma) \\ 0 & B(\sigma)S\sin\Delta(\sigma) & -B(\sigma)C\sin\Delta(\sigma) & B(\sigma)\cos\Delta(\sigma) \end{bmatrix} \quad (34)$$

where, $$A(\sigma) = \pm(P_f(\sigma)^2 - P_s(\sigma)^2),\ B(\sigma) = 2P_f(\sigma)P_s(\sigma),\ C = \cos 2\theta,\ S = \sin 2\theta \quad (35)$$

$P_f(\sigma)$ and $P_s(\sigma)$ respectively indicate the principal transmittances along the fast axis and the slow axis (f-axis and s-axis). $\theta$ indicates the direction of the fast axis (principal axis direction).

The retardation $\Delta(\sigma)$, the principal axis direction $\theta$, and the principal transmittances $P_f(\sigma)$ and $P_s(\sigma)$ along the fast axis and the slow axis are expressed as follows based on the expressions (34) and (35).

$$\theta = \frac{1}{2}\tan^{-1}\frac{m_{13}(\sigma)}{m_{32}(\sigma)}\ \text{or}\ \theta = \frac{1}{2}\tan^{-1}\frac{m_{02}(\sigma)}{m_{10}(\sigma)} \quad (36)$$

$$\Delta(\sigma) = \tan^{-1}\frac{\sqrt{m_{13}^2(\sigma) + m_{32}^2(\sigma)}}{m_{33}(\sigma)} \quad (37)$$

$$P_f(\sigma) = \sqrt{m_{00}(\sigma) + \sqrt{m_{10}^2(\sigma) + m_{02}^2(\sigma)}} \quad (38)$$

$$P_s(\sigma) = \sqrt{m_{00}(\sigma) - \sqrt{m_{10}^2(\sigma) + m_{02}^2(\sigma)}} \quad (39)$$

Specifically, the retardation, the principal axis direction, and the dichroism of the sample 100 can be calculated by utilizing the Mueller matrix elements of the sample 100.

5-3: Reflection Coefficient and Retardation

A Mueller matrix $M_{surf}(\sigma)$ relating to the reflection coefficient and the retardation in a primary scattering medium is expressed as follows.

$r_p(\sigma)$, $r_s(\sigma)$, and $\delta(\sigma)$ respectively indicate the amplitude reflection coefficients for p-polarized light and s-polarized light and the retardation between p-polarized light and s-polarized light.

The amplitude reflection coefficients $r_p(\sigma)$ and $r_s(\sigma)$, and the retardation $\delta(\sigma)$, are calculated as follows.

$$r_p(\sigma) = \sqrt{m_{00}(\sigma) + m_{01}(\sigma)} \quad (41)$$

$$r_s(\sigma) = \sqrt{m_{00}(\sigma) - m_{01}(\sigma)} \quad (42)$$

$$\delta(\sigma) = \tan^{-1}\frac{m_{23}(\sigma)}{m_{33}(\sigma)} \quad (43)$$

Specifically, the amplitude reflection coefficients for p-polarized light and s-polarized light and the retardation between p-polarized light and s-polarized light can be calculated by utilizing the Mueller matrix elements of the sample 100.

When the measuring apparatus according to the invention forms an optical characteristic element measurement unit that calculates these optical characteristic elements, the calculation device 60 (calculation section 50) may calculate these optical characteristic elements. In this case, the optical characteristic element measurement unit may be configured as a device that outputs the value of each optical characteristic element.

Modification

The measuring apparatus that calculates all of the sixteen Mueller matrix elements of the sample 100 has been described above. Note that the measuring apparatus according to the invention is not limited thereto.

(1) First Modification

The measuring apparatus may be configured to calculate a plurality of Mueller matrix elements by utilizing only one piece of light intensity information.

For example, when the principal axis directions of the polarizer 22, the first carrier retarder 24, the second carrier retarder 34, and the analyzer 32 of the optical system 10 are $$M_{surf}(\sigma) = \begin{bmatrix} r_p(\sigma)^2 + r_s(\sigma)^2 & r_p(\sigma)^2 - r_s(\sigma)^2 & 0 & 0 \\ r_p(\sigma)^2 - r_s(\sigma)^2 & r_p(\sigma)^2 + r_s(\sigma)^2 & 0 & 0 \\ 0 & 0 & 2r_p(\sigma)r_s(\sigma)\cos\delta(\sigma) & 2r_p(\sigma)r_s(\sigma)\sin\delta(\sigma) \\ 0 & 0 & -2r_p(\sigma)r_s(\sigma)\sin\delta(\sigma) & 2r_p(\sigma)r_s(\sigma)\cos\delta(\sigma) \end{bmatrix} \quad (40)$$

set at 45°, 0°, 0°, and 45°, nine Mueller matrix elements can be calculated, as is clear from the expressions (28a) to (28i).

The optical characteristics (e.g., retardation) of the sample 100 can be determined by utilizing all or some of the nine Mueller matrix elements (see the expressions (36) to (39) or the expressions (41) to (43)).

According to this modification, the optical characteristics of the sample 100 can be calculated based on the light intensity information relating to one type of measurement light. Specifically, necessary information can be obtained based on a small amount of data.

(2) Second Modification

The measuring apparatus may be configured to calculate fifteen or less Mueller matrix elements by utilizing a plurality of pieces of light intensity information.

For example, twelve Mueller matrix elements can be calculated by utilizing the expressions (28a) to (29i).

Alternatively, fifteen Mueller matrix elements can be calculated by utilizing the expressions (28a) to (30i).

The optical characteristics of the sample 100 can be determined by utilizing these Mueller matrix elements.

Second Embodiment

A second embodiment to which the invention is applied is described below while focusing on the difference from the first embodiment. Note that the above description is applied to this embodiment as far as possible.

(1) Mueller Matrix Element Calculation Principle of Measuring Apparatus According to this Embodiment The measuring apparatus 1 can derive nine relational expressions that indicate the relationship among the sixteen Mueller matrix elements based on the light intensity information obtained by one measurement and the principal axis direction information relating to the optical elements (see the expressions (8a) to (8i)), as described above.

When nine relational expressions include sixteen unknown quantities, it is normally impossible to calculate all of the sixteen unknown quantities. However, when nine relational expressions include nine or less unknown quantities, the unknown quantities can be calculated. Specifically, if nine relational expressions that indicate the relationship among nine Mueller matrix elements can be derived, the nine Mueller matrix elements can be calculated.

In the expressions (8a) to (8i), the Mueller matrix element is multiplied by one of the coefficients $A_{0000}$ to $A_{SS33}$. Therefore, if one of the coefficients $A_{0000}$ to $A_{SS33}$ is zero, the number of Mueller matrix elements that appear in the expressions (8a) to (8i) can be reduced.

The coefficients $A_{0000}$ to $A_{SS33}$ are values calculated by using the principal axis directions $\theta_P$, $\theta_1$, $\theta_2$, and $\theta_A$ of the four optical elements. Therefore, an Arbitrary coefficient among the coefficients $A_{0000}$ to $A_{SS33}$ can be selectively set at zero by adjusting the values $\theta_P$, $\theta_1$, $\theta_2$, and $\theta_A$ (i.e., the principal axis directions of the polarizer 22, the first carrier retarder 24, the second carrier retarder 34, and the analyzer 32). As a result, an arbitrary Mueller matrix element can be removed from the expressions (8a) to (8i). Specifically, nine relational expressions including only nine matrix elements among the sixteen Mueller matrix elements can be derived from the light intensity information obtained by one measurement by adjusting the principal axis directions of the polarizer 22, the first carrier retarder 24, the second carrier retarder 34, and the analyzer 32. Therefore, the nine Mueller matrix elements can be calculated by solving the nine relational expressions. Specifically, the nine Mueller matrix elements can be calculated from the light intensity information obtained by one measurement.

The coefficients $A_{0000}$ to $A_{SS33}$ change when the principal axis directions of the optical element change (see the expressions (9a) to (17)). Specifically, a different coefficient becomes zero by changing the principal axis directions of the optical elements, whereby nine relational expressions that indicate the relationship among different (nine) Mueller matrix elements can be derived. Accordingly, the remaining (nine) Mueller matrix elements can be calculated by solving these expressions.

The measuring apparatus according to this embodiment calculates all of the sixteen Mueller matrix elements by repeating the above-described operations. Specifically, the measuring apparatus according to this embodiment repeats the process that calculates the Mueller matrix elements by utilizing the light intensity information obtained by one measurement while changing the principal axis directions of the optical elements. This enables all of the sixteen Mueller matrix elements to be calculated.

Figure 9:
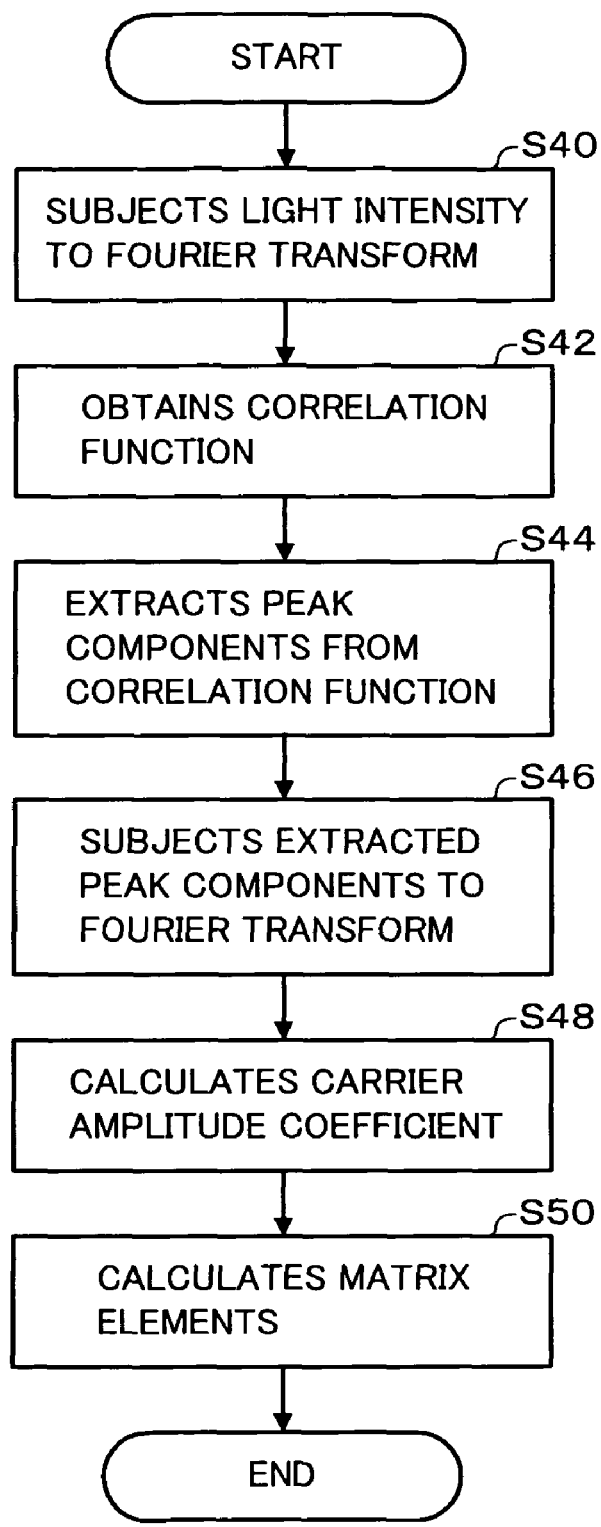
FIG. 9 is a flowchart illustrative of a matrix element calculation process.

(2) Mueller Matrix Element Calculation Process Performed by Measuring Apparatus According to this Embodiment FIG. 9 is a flowchart showing the operation of the measuring apparatus according to this embodiment (particularly the carrier amplitude coefficient calculation process and the Mueller matrix element calculation process).

In steps S40 to S48, the carrier amplitude coefficient is calculated from the light intensity information relating to the measurement light. The matrix element calculation process is then performed based on the carrier amplitude coefficient and the theoretical expression for the carrier amplitude coefficient (step S50).

The measuring apparatus according to this embodiment performs the matrix element calculation process based on the carrier amplitude coefficient calculated by the carrier amplitude coefficient calculation process corresponding to the measurement light. One or more matrix elements thus calculated are stored in the storage device 55.

The carrier amplitude coefficient calculation process and the matrix element calculation process (steps S40 to S50) are performed on the light intensity information relating to a plurality of measurement lights modulated by the optical system 10 in which setting of the principal axis direction of at least one optical element is changed. This enables all of the sixteen matrix elements to be calculated.

(3) Specific Mueller Matrix Element Calculation Example Using Measuring Apparatus According to this Embodiment The Mueller matrix element calculation process is described below while setting the principal axis directions of the optical elements (polarizer 22, first carrier retarder 24, second carrier retarder 34, and analyzer 32) of the optical system 10.

The principal axis directions of the polarizer 22, the first carrier retarder 24, the second carrier retarder 34, and the analyzer 32 of the optical system 10 are set at 45°, 0°, 0°, and −45°. In this case, the carrier amplitude coefficients are expressed as follows.

$$N_{00}(\sigma) = P_0(\sigma) m_{00}(\sigma) \tag{44a}$$

$$N_{C0}(\sigma) = P_0(\sigma) m_{02}(\sigma) \tag{44b}$$

$$N_{S0}(\sigma) = -P_0(\sigma) m_{03}(\sigma) \tag{44c}$$

$$N_{OC}(\sigma) = -P_0(\sigma)m_{20}(\sigma) \quad (44d)$$

$$N_{OS}(\sigma) = -P_0(\sigma)m_{30}(\sigma) \quad (44e)$$

$$N_{CC}(\sigma) = -P_0(\sigma)m_{22}(\sigma) \quad (44f)$$

$$N_{SC}(\sigma) = P_0(\sigma)m_{23}(\sigma) \quad (44g)$$

$$N_{CS}(\sigma) = -P_0(\sigma)m_{32}(\sigma) \quad (44h)$$

$$N_{SS}(\sigma) = P_0(\sigma)m_{33}(\sigma) \quad (44i)$$

The principal axis directions of the optical elements of the optical system 10 are then set at 45°, 0°, 45°, and 0°. In this case, the carrier amplitude coefficients are expressed as follows.

$$N_{00}(\sigma) = P_0(\sigma)m_{00}(\sigma) \quad (45a)$$

$$N_{C0}(\sigma) = P_0(\sigma)m_{02}(\sigma) \quad (45b)$$

$$N_{S0}(\sigma) = -P_0(\sigma)m_{03}(\sigma) \quad (45c)$$

$$N_{OC}(\sigma) = P_0(\sigma)m_{10}(\sigma) \quad (45d)$$

$$N_{OS}(\sigma) = -P_0(\sigma)m_{30}(\sigma) \quad (45e)$$

$$N_{CC}(\sigma) = P_0(\sigma)m_{12}(\sigma) \quad (45f)$$

$$N_{SC}(\sigma) = -P_0(\sigma)m_{13}(\sigma) \quad (45g)$$

$$N_{CS}(\sigma) = -P_0(\sigma)m_{32}(\sigma) \quad (45h)$$

$$N_{SS}(\sigma) = P_0(\sigma)m_{33}(\sigma) \quad (45i)$$

The principal axis directions of the optical elements of the optical system 10 are then set at 90°, 45°, 0°, and −45°. In this case, the carrier amplitude coefficients are expressed as follows.

$$N_{00}(\sigma) = P_0(\sigma)m_{00}(\sigma) \quad (46a)$$

$$N_{C0}(\sigma) = -P_0(\sigma)m_{01}(\sigma) \quad (46b)$$

$$N_{S0}(\sigma) = -P_0(\sigma)m_{03}(\sigma) \quad (46c)$$

$$N_{OC}(\sigma) = -P_0(\sigma)m_{20}(\sigma) \quad (46d)$$

$$N_{OS}(\sigma) = -P_0(\sigma)m_{30}(\sigma) \quad (46e)$$

$$N_{CC}(\sigma) = P_0(\sigma)m_{21}(\sigma) \quad (46f)$$

$$N_{SC}(\sigma) = P_0(\sigma)m_{23}(\sigma) \quad (46g)$$

$$N_{CS}(\sigma) = P_0(\sigma)m_{31}(\sigma) \quad (46h)$$

$$N_{SS}(\sigma) = P_0(\sigma)m_{33}(\sigma) \quad (46i)$$

The principal axis directions of the optical elements of the optical system 10 are then set at 90°, 45°, 45°, and 0°. In this case, the carrier amplitude coefficients are expressed as follows.

$$N_{00}(\sigma) = P_0(\sigma)m_{00}(\sigma) \quad (47a)$$

$$N_{C0}(\sigma) = -P_0(\sigma)m_{01}(\sigma) \quad (47b)$$

$$N_{S0}(\sigma) = -P_0(\sigma)m_{03}(\sigma) \quad (47c)$$

$$N_{OC}(\sigma) = P_0(\sigma)m_{10}(\sigma) \quad (47d)$$

$$N_{OS}(\sigma) = -P_0(\sigma)m_{30}(\sigma) \quad (47e)$$

$$N_{CC}(\sigma) = -P_0(\sigma)m_{11}(\sigma) \quad (47f)$$

$$N_{SC}(\sigma) = -P_0(\sigma)m_{13}(\sigma) \quad (47g)$$

$$N_{CS}(\sigma) = P_0(\sigma)m_{31}(\sigma) \quad (47h)$$

$$N_{SS}(\sigma) = P_0(\sigma)m_{33}(\sigma) \quad (47i)$$

The right side of each of the expressions (44a) to (47i) can be detected from the measured data. The left side of each of the expressions (44a) to (47i) is one of the Mueller matrix elements. Therefore, all of the sixteen Mueller matrix elements can be calculated using the expressions.

In this embodiment, the principal axis directions of the optical system 10 may be set under the following conditions. This simplifies the calculation process, whereby the processing speed of the measuring apparatus can be increased.

For example, the principal axis directions of the polarizer 22 and the first carrier retarder 24 may be set so that the angular difference in the principal axis direction is a multiple of 45° by an odd number. The principal axis directions of the second carrier retarder 34 and the analyzer 32 may be set so that the angular difference in the principal axis direction is a multiple of 45° by an odd number. The principal axis directions of the first carrier retarder 24 and the second carrier retarder 34 may be set so that the angular difference in the principal axis direction is a multiple of 45°.

Alternatively, the principal axis directions of the polarizer 22 and the first carrier retarder 24 may be set so that the angular difference in the principal axis direction is constant. The principal axis directions of the second carrier retarder 34 and the analyzer 32 may be set so that the angular difference in the principal axis direction is constant.

The invention is not limited to the above-described embodiments. Various modifications and variations may be made. The invention includes configurations substantially the same as the configurations described in the embodiments (in function, in method and effect, or in objective and effect). The invention also includes a configuration in which an unsubstantial section of the above-described embodiments is replaced by another section. The invention also includes a configuration having the same effects as those of the above-described configurations, or a configuration capable of achieving the same object as those of the above-described configurations. Further, the invention includes a configuration obtained by adding known technology to the above-described configurations.

For example, the measuring apparatus has been described which is configured so that light (e.g., white light) containing a band component is caused to be incident on the optical element, the measurement light containing the band component is dispersed into a spectrum, and the light intensity information is acquired corresponding to each wave number σ of the measurement light. Note that the invention may be applied to any method capable of acquiring the light intensity information (see FIG. 3A) corresponding to each wave number σ of the measurement light. In other words, the invention may be applied to any method capable of acquiring the modulated state of light corresponding to each wave number σ (wavelength) as the light intensity information. For example, a configuration may be employed in which the light intensity information relating to a given band component of the measurement light is acquired without dispersing the measurement light into a spectrum, by continuously emitting light (monochromatic light) with a specific wave number (wavelength) while changing the wave number (wavelength). In this case, the measuring apparatus may include a spectroscopic section that disperses white light into a spectrum between the light source 12 and the polarizer 22. Alternatively, a light-emitting device capable of continuously emitting light with a different wavelength (wave number) may be used as the light source.

The principal axis direction of the optical element of the optical system 10 may be changed manually. In this case, the calculation process may be performed based on the principal axis direction information acquired by a detection section.

INDUSTRIAL APPLICABILITY

The invention can be utilized for evaluation of organic polymer materials such as a liquid crystal and research and development of new materials. The invention can also be applied to quality control of a polymer orientation state. Findings obtained therefrom are very effective for development of new materials.

Moreover, the invention makes it possible to inspect inorganic materials such as semiconductors and optical crystals and measure the photoelastic constant and the stress distribution occurring in the materials.

The invention can also be applied to biotechnology in addition to the above-described organic and inorganic polymer materials.

The invention claimed is:

1. A measuring apparatus that calculates at least one matrix element among sixteen matrix elements of a Mueller matrix that indicates optical characteristics of a measurement target, the measuring apparatus comprising:
a light intensity information acquisition section that acquires light intensity information relating to a measurement light containing a given band component, the measurement light having been modulated by at least four optical elements included in an optical system and the measurement target; and
a calculation section that calculates the at least one matrix element based on the light intensity information relating to the measurement light and a theoretical expression for the light intensity of the measurement light,
the at least four optical elements including a first polarizer, a second polarizer, a first carrier retarder, and a second carrier retarder, the first and second carrier retarders having retardations that are known and differ from each other;
the measurement light being obtained by causing a light emitted from a light source to be incident on the measurement target through the first polarizer and the first carrier retarder and causing the light modulated by the measurement target to be incident on a light-receiving section through the second carrier retarder and the second polarizer;
the light intensity information acquisition section acquiring the light intensity information relating to a plurality of the measurement lights obtained from the optical system by changing setting of a principal axis direction of at least one of the at least four optical elements; and
the calculation section performing:
a carrier amplitude coefficient calculation process that calculates at least one carrier amplitude coefficient included in the theoretical expression for the light intensity of each of the measurement lights based on a correlation function obtained by analyzing the light intensity information relating to each of the measurement lights; and
a matrix element calculation process that calculates the at least one matrix element based on the carrier amplitude coefficient calculated by the carrier amplitude coefficient calculation process and the theoretical expression for the carrier amplitude coefficient including the principal axis directions of the at least four optical elements and the at least one matrix element.

2. The measuring apparatus as defined in claim 1, wherein the calculation section performs the matrix element calculation process based on the carrier amplitude coefficients calculated by the carrier amplitude coefficient calculation process on a plurality of the measurement lights.

3. The measuring apparatus as defined in claim 1, wherein the calculation section performs the matrix element calculation process based on the carrier amplitude coefficient calculated by the carrier amplitude coefficient calculation process on each of the measurement lights.

4. The measuring apparatus as defined in claim 1, wherein the calculation section calculates all of the sixteen matrix elements.

5. The measuring apparatus as defined in claim 1, wherein the light intensity information acquisition section acquires the light intensity information relating to the measurement lights obtained from the optical system by changing the setting of the principal axis direction of at least one of the first polarizer and the first carrier retarder.

6. The measuring apparatus as defined in claim 5, wherein the light intensity information acquisition section acquires the light intensity information relating to a plurality of the measurement lights obtained from the optical system set to have a constant angular difference in the principal axis direction between the first polarizer and the first carrier retarder.

7. The measuring apparatus as defined in claim 1, wherein the light intensity information acquisition section acquires the light intensity information relating to a plurality of the measurement lights obtained from the optical systems by changing the setting of the principal axis direction of at least one of the second polarizer and the second carrier retarder.

8. The measuring apparatus as defined in claim 7, wherein the light intensity information acquisition section acquires the light intensity information relating to a plurality of the measurement lights obtained from the optical system set to have a constant angular difference in the principal axis direction between the second polarizer and the second carrier retarder.

9. The measuring apparatus as defined in claim 1, wherein the light intensity information acquisition section acquires the light intensity information relating to the measurement light obtained from the optical system that is set so that the angular difference in the principal axis direction between the at least four optical elements is a multiple of 45°.

10. The measuring apparatus as defined in claim 9, wherein the light intensity information acquisition section acquires the light intensity information relating to the measurement light obtained from the optical system set so that the angular difference in the principal axis direction between the first polarizer and the first carrier retarder is a multiple of 45° by an odd number, the angular difference in the principal axis direction between the second polarizer and the second carrier retarder is a multiple of 45° by an odd number, and the angular difference in the principal axis direction between the first carrier retarder and the second carrier retarder is a multiple of 45°.

11. The measuring apparatus as defined in claim 1, further comprising:
a detection section that detects principal axis direction information relating to the at least four optical elements, wherein the calculation section performs the carrier amplitude coefficient calculation process by utilizing the principal axis direction information detected by the detection section.

12. The measuring apparatus as defined claim 1, further comprising:
an actuator that changes the principal axis direction of at least one of the at least four optical elements.

13. The measuring apparatus as defined in claim 1,
wherein the light emitted from the light source contains a given band component.

14. An optical characteristic measurement unit comprising the measuring apparatus as defined claim 1.

15. A measuring apparatus that calculates at least one matrix element among sixteen matrix elements of a Mueller matrix that indicates optical characteristics of a measurement target, the measuring apparatus comprising:
an optical system that includes a light source, at least four optical elements, and a light-receiving section that receives a measurement light modulated by the at least four optical elements and the measurement target;
a light intensity information acquisition section that acquires light intensity information relating to the measurement light containing a given band component; and
a calculation section that calculates the at least one matrix element based on the light intensity information relating to the measurement light and a theoretical expression for the light intensity of the measurement light,
the at least four optical elements including a first polarizer, a second polarizer, a first carrier retarder, and a second carrier retarder, the first and second carrier retarders having retardations that are known and differ from each other;
the optical system causing a light emitted from the light source to be incident on the measurement target through the first polarizer and the first carrier retarder and causing the light modulated by the measurement target to be incident on the light-receiving section through the second carrier retarder and the second polarizer;
the optical system enabling a principal axis direction of at least one of the at least four optical elements to be changed;
the light intensity information acquisition section acquiring the light intensity information relating to a plurality of the measurement lights obtained from the optical system by changing setting of the principal axis direction of at least one of the at least four optical elements; and
the calculation section performing:
a carrier amplitude coefficient calculation process that calculates at least one carrier amplitude coefficient included in the theoretical expression for the light intensity of each of the measurement lights based on a correlation function obtained by analyzing the light intensity information relating to each of the measurement lights; and
a matrix element calculation process that calculates the at least one matrix element based on the carrier amplitude coefficient calculated by the carrier amplitude coefficient calculation process and the theoretical expression for the carrier amplitude coefficient including the principal axis directions of the at least four optical elements and the at least one matrix element.

16. A measuring method for calculating at least one matrix element among sixteen matrix elements of a Mueller matrix that indicates optical characteristics of a measurement target, the measuring method comprising:

a light intensity information acquisition step that acquires light intensity information relating to a measurement light containing a given band component, the measurement light having been modulated by at least four optical elements included in an optical system and the measurement target; and
a calculation step that calculates the at least one matrix element based on the light intensity information relating to the measurement light and a theoretical expression for the light intensity of the measurement light,
the at least four optical elements including a first polarizer, a second polarizer, a first carrier retarder, and a second carrier retarder, the first and second carrier retarders having retardations that are known and differ from each other;
the measurement light being obtained by causing a light emitted from a light source to be incident on the measurement target through the first polarizer and the first carrier retarder and causing the light modulated by the measurement target to be incident on a light-receiving section through the second carrier retarder and the second polarizer;
the light intensity information acquisition step acquiring the light intensity information relating to a plurality of the measurement lights obtained from the optical system by changing setting of a principal axis direction of at least one of the at least four optical elements; and
the calculation step including:
a carrier amplitude coefficient calculation process that calculates at least one carrier amplitude coefficient included in the theoretical expression for the light intensity of each of the measurement lights based on a correlation function obtained by analyzing the light intensity information relating to each of the measurement lights; and
a matrix element calculation process that calculates the at least one matrix element based on the carrier amplitude coefficient calculated by the carrier amplitude coefficient calculation process and the theoretical expression for the carrier amplitude coefficient including the principal axis directions of the at least four optical elements and the at least one matrix element.

17. The measuring method as defined in claim 16,
wherein, in the calculation step, the matrix element calculation process is performed based on the carrier amplitude coefficients calculated by the carrier amplitude coefficient calculation process on a plurality of the measurement lights.

18. The measuring method as defined in claim 16,
wherein, in the calculation step, the matrix element calculation process is performed based on the carrier amplitude coefficient calculated by the carrier amplitude coefficient calculation process on each of the measurement lights.

19. The measuring method as defined in claim 16,
wherein the calculation step calculates all of the sixteen matrix elements.

20. The measuring method as defined in claim 16,
wherein the light emitted from the light source contains a given band component.

21. A measuring apparatus that calculates nine matrix elements among sixteen matrix elements of a Mueller matrix that indicates optical characteristics of a measurement target, the measuring apparatus comprising:
a light intensity information acquisition section that acquires light intensity information relating to a measurement light containing a given band component, the measurement light having been modulated by at least four optical elements included in an optical system and the measurement target, the at least four optical elements being set to have a given angular difference in principal axis direction; and a calculation section that calculates the nine matrix elements based on the light intensity information relating to the measurement light and a theoretical expression for the light intensity of the measurement light, the at least four optical elements including a first polarizer, a second polarizer, a first carrier retarder, and a second carrier retarder, the first and second carrier retarders having retardations that are known and differ from each other;

the measurement light being obtained by causing a light emitted from a light source to be incident on the measurement target through the first polarizer and the first carrier retarder and causing the light modulated by the measurement target to be incident on a light-receiving section through the second carrier retarder and the second polarizer; and the calculation section performing:

a carrier amplitude coefficient calculation process that calculates all of nine carrier amplitude coefficients included in the theoretical expression for the light intensity of the measurement light based on a correlation function obtained by analyzing the light intensity information; and a matrix element calculation process that calculates the nine matrix elements based on the nine carrier amplitude coefficients calculated by the carrier amplitude coefficient calculation process and the theoretical expression for the carrier amplitude coefficients including the principal axis directions of the at least four optical elements and the nine matrix elements.

22. A measuring apparatus that calculates nine matrix elements among sixteen matrix elements of a Mueller matrix that indicates optical characteristics of a measurement target, the measuring apparatus comprising:

an optical system that includes a light source, at least four optical elements, and a light-receiving section that receives a measurement light modulated by the at least four optical elements and the measurement target;

a light intensity information acquisition section that acquires light intensity information relating to the measurement light containing a given band component; and a calculation section that calculates the nine matrix elements based on the light intensity information relating to the measurement light and a theoretical expression for the light intensity of the measurement light, the at least four optical elements including a first polarizer, a second polarizer, a first carrier retarder, and a second carrier retarder, the first and second carrier retarders having retardations that are known and differ from each other;

the optical system causing a light emitted from the light source to be incident on the measurement target through the first polarizer and the first carrier retarder and causing the light modulated by the measurement target to be incident on the light-receiving section through the second carrier retarder and the second polarizer;

the optical system being set so that the four optical elements have a given angular difference in principal axis direction; and the calculation section performing:

a carrier amplitude coefficient calculation process that calculates all of nine carrier amplitude coefficients included in the theoretical expression for the light intensity of the measurement light based on a correlation function obtained by analyzing the light intensity information; and a matrix element calculation process that calculates the nine matrix elements based on the nine carrier amplitude coefficients calculated by the carrier amplitude coefficient calculation process and the theoretical expression for the carrier amplitude coefficients including the principal axis directions of the at least four optical elements and the nine matrix elements.

23. A measuring method for calculating nine matrix elements among sixteen matrix elements of a Mueller matrix that indicates optical characteristics of a measurement target, the measuring method comprising:

a light intensity information acquisition step that acquires light intensity information relating to a measurement light containing a given band component, the measurement light having been modulated by at least four optical elements included in an optical system and the measurement target, the at least four optical elements being set to have a given angular difference in principal axis direction; and a calculation step that calculates the nine matrix elements based on the light intensity information relating to the measurement light and a theoretical expression for the light intensity of the measurement light, the at least four optical elements including a first polarizer, a second polarizer, a first carrier retarder, and a second carrier retarder, the first and second carrier retarders having retardations that are known and differ from each other;

the measurement light being obtained by causing a light emitted from a light source to be incident on the measurement target through the first polarizer and the first carrier retarder and causing the light modulated by the measurement target to be incident on a light-receiving section through the second carrier retarder and the second polarizer; and the calculation step including:

a carrier amplitude coefficient calculation process that calculates all of nine carrier amplitude coefficients included in the theoretical expression for the light intensity of the measurement light based on a correlation function obtained by analyzing the light intensity information; and a matrix element calculation process that calculates the nine matrix elements based on the nine carrier amplitude coefficients calculated by the carrier amplitude coefficient calculation process and the theoretical expression for the carrier amplitude coefficients including the principal axis directions of the at least four optical elements and the nine matrix elements.

24. A measuring apparatus that calculates all of sixteen matrix elements of a Mueller matrix that indicates optical characteristics of a measurement target, the measuring apparatus comprising:

a light intensity information acquisition section that acquires light intensity information relating to a measurement light containing a given band component, the measurement light having been modulated by a plurality of optical elements included in an optical system and the measurement target; and a calculation section that calculates all of the sixteen matrix elements based on the light intensity information relating to the measurement light and a theoretical expression for the light intensity of the measurement light, the light intensity information acquisition section acquiring the light intensity information relating to a plurality of the measurement lights obtained from the optical system by changing setting of a principal axis direction of at least one of the optical elements; and the calculation section performing:

a carrier amplitude coefficient calculation process that calculates at least one carrier amplitude coefficient included in the theoretical expression for the light intensity of each of the measurement lights based on a correlation function obtained by analyzing the light intensity information relating to each of the measurement lights; and a matrix element calculation process that calculates all of the sixteen matrix elements based on the carrier amplitude coefficient calculated by the carrier amplitude coefficient calculation process and the theoretical expression for the carrier amplitude coefficient including the principal axis directions of a plurality of the optical elements and at least one of the matrix elements.

25. A measuring method for calculating all of sixteen matrix elements of a Mueller matrix that indicates optical characteristics of a measurement target, the measuring method comprising:

a light intensity information acquisition step that acquires light intensity information relating to a measurement light containing a given band component, the measurement light having been modulated by a plurality of optical elements included in an optical system and the measurement target; and a calculation step that calculates the sixteen matrix elements based on the light intensity information relating to the measurement light and a theoretical expression for the light intensity of the measurement light, the light intensity information acquisition step acquiring the light intensity information relating to a plurality of the measurement lights obtained from the optical system by changing setting of a principal axis direction of at least one of the optical elements; and the calculation step including:

a carrier amplitude coefficient calculation process that calculates at least one carrier amplitude coefficient included in the theoretical expression for the light intensity of each of the measurement lights based on a correlation function obtained by analyzing the light intensity information relating to each of the measurement lights; and a matrix element calculation process that calculates all of the sixteen matrix elements based on the carrier amplitude coefficients calculated by the carrier amplitude coefficient calculation process and the theoretical expression for the carrier amplitude coefficient including the principal axis directions of the optical elements and at least one of the matrix elements.

* * * * *